US011684574B2

(12) United States Patent
Fedorchak et al.

(10) Patent No.: US 11,684,574 B2
(45) Date of Patent: Jun. 27, 2023

(54) ARTIFICIAL CELLS AND DELIVERY DEVICES FOR USE IN TISSUE ENGINEERING, AND RELATED METHODS

(71) Applicant: University of Pittsburgh—Of the Commonwealth System of Higher Education, Pittsburgh, PA (US)

(72) Inventors: Morgan Virginia Fedorchak, Mars, PA (US); Jeffrey Krawiec, Levittown, PA (US); Steven R. Little, Allison Park, PA (US); Katherine Lorentz, Pittsburgh, PA (US); David A. Vorp, Pittsburgh, PA (US); Justin Weinbaum, Allison Park, PA (US)

(73) Assignees: University of Pittsburgh—Of the Commonwealth System of Higher Education, Pittsburgh, PA (US); System of Higher Education 1tts, Urgh (PA)

( * ) Notice: Subject to any disclaimer, the term of this patent is extended or adjusted under 35 U.S.C. 154(b) by 1165 days.

(21) Appl. No.: 16/308,889

(22) PCT Filed: Jun. 29, 2017

(86) PCT No.: PCT/US2017/039973
§ 371 (c)(1),
(2) Date: Dec. 11, 2018

(87) PCT Pub. No.: WO2018/005780
PCT Pub. Date: Jan. 4, 2018

(65) Prior Publication Data
US 2019/0336444 A1    Nov. 7, 2019

Related U.S. Application Data

(60) Provisional application No. 62/356,754, filed on Jun. 30, 2016.

(51) Int. Cl.
| A61L 27/50 | (2006.01) |
| A61L 27/56 | (2006.01) |
| A61L 27/58 | (2006.01) |
| A61K 9/107 | (2006.01) |
| A61K 9/00 | (2006.01) |
| A61K 9/16 | (2006.01) |
| A61K 35/15 | (2015.01) |
| A61K 35/28 | (2015.01) |
| A61K 35/34 | (2015.01) |
| A61K 35/39 | (2015.01) |
| C12N 5/071 | (2010.01) |

(52) U.S. Cl.
CPC .......... *A61K 9/1075* (2013.01); *A61K 9/0004* (2013.01); *A61K 9/1647* (2013.01); *A61K 35/15* (2013.01); *A61K 35/28* (2013.01); *A61K 35/34* (2013.01); *A61K 35/39* (2013.01); *A61L 27/507* (2013.01); *A61L 27/56* (2013.01); *A61L 27/58* (2013.01); *C12N 5/0691* (2013.01); *A61L 2300/602* (2013.01); *A61L 2300/62* (2013.01); *C12N 2533/40* (2013.01)

(58) Field of Classification Search
None
See application file for complete search history.

(56) References Cited

U.S. PATENT DOCUMENTS

| 8,101,167 | B2 | 1/2012 | Gueniche |
| 8,765,182 | B2 | 7/2014 | Day et al. |
| 8,911,963 | B2 | 12/2014 | Epstein et al. |
| 9,029,146 | B2 | 5/2015 | Lim et al. |
| 9,617,515 | B2 | 4/2017 | Young et al. |
| 2007/0292401 | A1 | 12/2007 | Harmon et al. |
| 2009/0275129 | A1* | 11/2009 | Cooper .................. C12M 21/08 435/366 |
| 2011/0177015 | A1 | 7/2011 | Friedlander |
| 2012/0172456 | A1* | 7/2012 | Little ....................... G16B 5/30 514/772.3 |
| 2012/0195969 | A1 | 8/2012 | Riordan et al. |
| 2012/0207705 | A1 | 8/2012 | Kara |
| 2012/0276215 | A1 | 11/2012 | Riordan et al. |
| 2012/0294949 | A1 | 11/2012 | Johnstone et al. |
| 2014/0377366 | A1 | 12/2014 | Krebs |
| 2015/0023911 | A1 | 1/2015 | Schilling et al. |
| 2015/0064273 | A1 | 3/2015 | Peled et al. |

FOREIGN PATENT DOCUMENTS

| WO | 2006029262 A2 | 3/2006 |
| WO | 2007100845 A2 | 9/2007 |
| WO | 2007149861 A2 | 12/2007 |
| WO | 2008020815 A1 | 2/2008 |
| WO | 2008155558 A2 | 12/2008 |
| WO | 2010038232 A1 | 4/2010 |
| WO | 2011033260 A1 | 3/2011 |
| WO | 2011127090 A1 | 10/2011 |
| WO | 2012047733 A2 | 4/2012 |
| WO | 2013113821 A1 | 8/2013 |

OTHER PUBLICATIONS

Ansary et al, Trop J Pharm Res, Jul. 2014, 13(7):1179-1190. (Year: 2014).*

(Continued)

*Primary Examiner* — Allison M Fox
(74) *Attorney, Agent, or Firm* — The Webb Law Firm

(57) ABSTRACT

Provided herein is a drug delivery device and composition, such as a particle, comprising conditioned medium. Also provided herein is a method of preparing polymeric particles for release of conditioned medium. Further, a tissue growth scaffold comprising particles for release of conditioned medium is provided.

17 Claims, 7 Drawing Sheets

(56) References Cited

OTHER PUBLICATIONS

Inukai et al, Biochem Biophys Res Comm, 2013, 430:763-768. (Year: 2013).*
Tran et al, Adv Drug Deliv Rev, 2015, 82-83: 1-11. (Year: 2015).*
Liu, "Prevention of focal intimal hyperplasia in rat vein grafts by using a tissue engineering approach", Atherosclerosis, 1998, pp. 365-377, vol. 140.
Liu et al., "Strategies to Optimize Adult Stem Cell Therapy for Tissue Regeneration", International Journal of Molecular Sciences, 2016, 16 pages, vol. 17, No. 6.
Lloyd-Jones et al., "Heart Disease and Stroke Statistics—2009 Update A Report From the American Heart Association Statistics Committee and Stroke Statistics Subcommittee", Circulation, 2009, pp. 480-486, vol. 119.
Lopatina et al., "Adipose-Derived Stem Cells Stimulate Regeneration of Peripheral Nerves: BDNF Secreted by These Cells Promotes Nerve Healing and Axon Growth De Novo", PLoS ONE, 2011, vol. 6, No. 3, Article No. e17899.
Lovett et al., "Tubular silk scaffolds for small diameter vascular grafts" Organogenesis, 2010, pp. 217-224, vol. 6, No. 4.
Madonna et al., "Age-dependent impairment of number and angiogenic potential of adipose tissue-derived progenitor cells", European journal of clinical investigation, 2011, pp. 127-133, vol. 41.
Matsumara et al., "First Evidence That Bone Marrow Cells Contribute to the Construction of Tissue-Engineered Vascular Autografts In Vivo", Circulation, 2003, pp. 1729-1734, vol. 108.
Matsumara et al., "Evaluation of Tissue-Engineered Vascular Autografts", Tissue Engineering, 2006, pp. 3075-3083, vol. 12, No. 11.
Mcclellan, "Guest Editorial: Epidemic End-Stage Renal Disease in the United States", Artificial Organs, 1994, pp. 413-415, vol. 18, No. 3.
Melchiorri et al., "Development and assessment of a biodegradable solvent cast polyester fabric small-diameter vascular graft", Journal of Biomedical Materials Research Part A, 2014, pp. 1972-1981, vol. 102, No. 6.
Mirensky et al., "Tissue-engineered vascular grafts: Does cell seeding matter?", Journal of Pediatric Surgery, 2010, pp. 1299-1305, vol. 45.
Moon et al., "The Effect of Secretory Factors of Adipose-Derived Stem Cells on Human Keratinocytes", International Journal of Molecular Sciences, 2012, pp. 1239-1257, vol. 13.
Mooney et al., "Localized Delivery of Epidermal Growth Factor Improves the Survival of Transplanted Hepatocytes", Biotechnology and Bioengineering, 1996, pp. 422-429, vol. 50.
Naito et al., "Characterization of the Natural History of Extracellular Matrix Production in Tissue-Engineered Vascular Grafts during Neovessel Formation", Cells Tissues Organs, 2012, pp. 60-72, vol. 195.
Naito et al., "Beyond Burst Pressure: Initial Evaluation of the Natural History of the Biaxial Mechanical Properties of Tissue-Engineered Vascular Grafts in the Venous Circulation Using a Murine Model", Tissue Engineering: Part A, 2014, pp. 346-355, vol. 20, Nos. 1 and 2.
Neff et al., "Vascular smooth muscle enhances functionality of tissue-engineered blood vessels in vivo", Journal of Vascular Surgery, 2011, pp. 426-434, vol. 53.
Nelson et al., "Functional Small-Diameter Human Tissue-Engineered Arterial Grafts in an Immunodeficient Mouse Model: Preliminary Findings" Archives of Surgery, 2008, pp. 488-494, vol. 143, No. 5.
Nieponice et al., "Development of a tissue-engineered vascular graft combining a biodegradable scaffold, muscle-derived stem cells and a rotational vacuum seeding technique", Biomaterials, 2008, pp. 825-833, vol. 29.
Nieponice et al., "In Vivo Assessment of a Tissue-Engineered Vascular Graft Combining a Biodegradable Elastomeric Scaffold and Muscle-Derived Stem Cells in a Rat Model", Tissue Engineering: Part A, 2010, pp. 1215-1223, vol. 16, No. 4.
Niklason et al., "Functional Arteries Grown in Vitro", Science, 1999, pp. 489-493, vol. 284.
Olausson et al., "Transplantation of an allogeneic vein bioengineered with autologous stem cells: a proof-of-concept study", The Lancet, 2012, pp. 230-237, vol. 380.
Otrock et al., "Understanding the biology of angiogenesis: Review of the most important molecular mechanisms", Blood Cells, Molecules, & Diseases, 2007, pp. 212-220, vol. 39.
Pavcnik et al., "Angiographic Evaluation of Carotid Artery Grafting with Prefabricated Small-Diameter, Small-Intestinal Submucosa Grafts in Sheep", Cardiovascular and Interventional Radiology, 2009, pp. 106-113, vol. 32, No. 1.
Pezzone et al., "Investigating Why Adipose-Derived Stem Cells from Diabetic Patients Display a Pro-Thrombogenic Phenotype", Department of Bioengineering BIOE 1002 Technical Symposium, 2014, 4 pages.
Pezzone et al., "Seeding of Microspheres into a Porous Tubular Scaffold as a Tissue Engineered Vascular Graft", BMES Annual Meeting, 2015, 1 page.
Pezzone et al., "Adipose-Derived Stem Cells from Diabetic Patients Display a Prothrombogenic Phenotype", Ingenium—Undergraduate Journal of the Swanson School of Engineering at the University of Pittsburgh, 2015, pp. 72-76.
Policha et al., "Endothelial differentiation of diabetic adipose-derived stem cells", Journal of Surgical Research, 2014, pp. 656-663, vol. 192.
Quint et al., "Decellularized tissue-engineered blood vessel as an arterial conduit", PNAS, 2011, pp. 9214-9219, vol. 108, No. 22.
Quint et al., "Allogeneic human tissue-engineered blood vessel", Journal of Vascular Surgery, 2012, pp. 790-798, vol. 55.
Ramazani et al., "Formulation and characterization of microspheres loaded with imatinib for sustained delivery", International Journal of Pharmaceutics, 2015, pp. 123-130, vol. 482.
Rehman et al., "Secretion of Angiogenic and Antiapoptotic Factors by Human Adipose Stromal Cells", Circulation, 2004, pp. 1292-1298, vol. 109.
Richardson et al., "Polymeric system for dual growth factor delivery", Nature Biotechnology, 2001, pp. 1029-1034, vol. 19.
Robb, "The Role of Micro-Embolism in the Production of Irreversible Shock", Annals of Surgery, 1963, vol. 158, No. 4.
Roh et al., "Construction of an autologous tissue-engineered venous conduit from bone marrow-derived vascular cells: Optimization of cell harvest and seeding techniques", Journal of Pediatric Surgery, 2007, pp. 198-202, vol. 42.
Roh et al., "Tissue-engineered vascular grafts transform into mature blood vessels via an inflammation-mediated process of vascular remodeling", PNAS, 2010, pp. 4669-4674, vol. 107, No. 10.
Rothstein et al., "A simple model framework for the prediction of controlled release from bulk eroding polymer matrices", Journal of Materials Chemistry, 2008, pp. 1873-1880, vol. 18.
Rothstein et al., "A unified mathematical model for the prediction of controlled release from surface and bulk eroding polymer matrices", Biomaterials, 2009, pp. 1657-1664, vol. 30.
Rothstein et al., "A "tool box" for rational design of degradable controlled release formulations", Journal of Materials Chemistry, 2011, pp. 29-39, vol. 21.
Rothstein et al., "A Retrospective Mathematical Analysis of Controlled Release Design and Experimentation", Molecular Pharmaceutics, 2012, pp. 3003-3011, vol. 9.
Rui et al., "Controlled release of vascular endothelial growth factor using poly-lactic-co-glycolic acid microspheres: In vitro characterization and application in polycaprolactone fumarate nerve conduits", Acta Biomaterialia, 2012, pp. 511-518, vol. 8.
Schinkothe et al., "In Vitro Secreting Profile of Human Mesenchymal Stem Cells", Stem Cells and Development, 2008, pp. 199-205, vol. 17.
Schipper et al., "Regional Anatomic and Age Effects on Cell Function of Human Adipose-Derived Stem Cells", Annals of Plastic Surgery, 2008, pp. 538-544, vol. 60, No. 5.
Schlich et al., "VEGF in the Crosstalk between Human Adipocytes and Smooth Muscle Cells: Depot-Specific Release from Visceral and Perivascular Adipose Tissue", Mediators of Inflammation, 2013, 10 pages, Article No. 982458.

(56) References Cited

OTHER PUBLICATIONS

Schwendeman, "Recent Advances in the Stabilization of Proteins Encapsulated in Injectable PLGA Delivery Systems", Critical Reviews™ in Therapeutic Drug Carrier Systems, 2002, pp. 73-98, vol. 19, No. 1.
Shi et al., "Utilizing Granulocyte Colony-stimulating Factor to Enhance Vascular Graft Endothelialization from Circulating Blood Cells", Annals of Vascular Surgery, 2002, pp. 314-320, vol. 16.
Shin et al., "Mussel-Inspired Immobilization of Vascular Endothelial Growth Factor (VEGF) for Enhanced Endothelialization of Vascular Grafts", Biomacromolecules, 2012, pp. 2020-2028, vol. 13.
Skop et al., "Heparin crosslinked chitosan microspheres for the delivery of neural stem cells and growth factors for central nervous system repair", Acta Biomaterialia, 2013, pp. 6834-6843, vol. 9.
Soletti et al., "A seeding device for tissue engineered tubular structures", Biomaterials, 2006, pp. 4863-4870, vol. 27.
Soletti et al., "Development of a Stem Cell-Based Tissue Engineered Vascular Graft", 2008, Bioengineering PhD Thesis, 404 pages, University of Pittsburgh, Pittsburgh, Pennsylvania.
Soletti et al., "A bilayered elastomeric scaffold for tissue engineering of small diameter vascular grafts", Acta Biomaterialia, 2010, pp. 110-122, vol. 6.
Acosta et al., "Adipose Mesenchymal Stromal Cells Isolated From Type 2 Diabetic Patients Display Reduced Fibrinolytic Activity", Diabetes, 2013, pp. 4266-4269, vol. 62.
Ahmann et al., "Fibrin Degradation Enhances Vascular Smooth Muscle Cell Proliferation and Matrix Deposition in Fibrin-Based Tissue Constructs Fabricated In Vitro", Tissue Engineering: Part A, 2010, pp. 3261-3270, vol. 16, No. 10.
Arshady, "Microspheres and Microcapsules, a Survey of Manufacturing Techniques: Part III: Solvent Evaporation", Polymer Engineering and Science, 1990, pp. 915-924, vol. 30, No. 15.
Athanasiou et al., "Sterilization, toxicity, biocompatibility and clinical applications of polylactic acid/polyglycolic acid copolymers", Biomaterials, 1996, pp. 93-102, vol. 17.
Balmert et al., "Biomimetic Delivery with Micro-and Nanoparticles", Advanced Materials, 2012, pp. 3757-3778, vol. 24.
Barleon et al., "Migration of Human Monocytes in Response to Vascular Endothelial Growth Factor (VEGF) Is Mediated via the VEGF Receptor flt-1", Blood, 1996, pp. 3336-3343, vol. 87, No. 8.
Basaran et al., "Complications and Long-Term Follow-up of 4416 Vascular Access Procedures", Transplantation Proceedings, 2003, pp. 2578-2579, vol. 35.
Basmanav et al., "Sequential growth factor delivery from complexed microspheres for bone tissue engineering", Biomaterials, 2008, pp. 4195-4204, vol. 29.
Blaber et al., "Analysis of in vitro secretion profiles from adipose-derived cell populations", Journal of Translational Medicine, 2012, 16 pages, vol. 10.
Brennan et al., "Tissue-engineered Vascular Grafts Demonstrate Evidence of Growth and Development When Implanted in a Juvenile Animal Model", Annals of Surgery, 2008, pp. 370-377, vol. 248, No. 3.
Byeon et al., "PEGylated apoptotic protein-loaded PLGA microspheres for cancer therapy", International Journal of Nanomedicine, 2015, pp. 739-748, vol. 10.
Cheleuitte et al., "In Vitro Secretion of Cytokines by Human Bone Marrow: Effects of Age and Estrogen Status", Journal of Clinical Endocrinology and Metabolism, 1998, pp. 2043-2051, vol. 83, No. 6.
Chen et al., "In vitro cellular responses to scaffolds containing two microencapulated growth factors", Biomaterials, 2009, pp. 5215-5224, vol. 30.
Cherubino et al., "Adipose-Derived Stem Cells for Wound Healing Applications", Annals of Plastic Surgery, 2011, pp. 210-215, vol. 66, No. 2.
Cho et al., "Small-Diameter Blood Vessels Engineered With Bone Marrow-Derived Cells", Annals of Surgery, 2005, pp. 506-515, vol. 241, No. 3.
Cho et al., "Enhancement of in vivo endothelialization of tissue-engineered vascular grafts by granulocyte colony-stimulating factor", Journal of Biomedical Materials Research. Part A, 2006, pp. 252-263, vol. 76, No. 2.
Cho et al., "Evidence for In Vivo Growth Potential and Vascular Remodeling of Tissue-Engineered Artery", Tissue Engineering: Part A, 2009, pp. 901-912, vol. 15, No. 4.
Choi et al., "Injectable PLGA microspheres encapsulating WKYMVM peptide for neovascularization", Acta Biomaterialia, 2015, pp. 76-85, vol. 25.
Cianfarani et al., "Diabetes impairs adipose tissue-derived stem cell function and efficiency in promoting wound healing", Wound Repair and Regeneration, 2013, pp. 545-553, vol. 21.
Courtney et al., "Design and analysis of tissue engineering scaffolds that mimic soft tissue mechanical anisotropy", Biomaterials, 2006, pp. 3631-3638, vol. 27.
Cummings et al., "Tissue-engineered vascular graft remodeling in a growing lamb model: expression of matrix metalloproteinases", European Journal of Cardio-Thoracic Surgery, 2012, pp. 167-172, vol. 41.
Dahl et al., "Readily Available Tissue-Engineered Vascular Grafts", Science Translational Medicine, 2011, vol. 3, Issue 68, Article No. 68ra9.
De Boer et al., "Short-and long-term peripheral nerve regeneration using a poly-lactic-co-glycolic-acid scaffold containing nerve growth factor and glial cell line-derived neurotrophic factor releasing microspheres", Journal of Biomedical Materials Research Part A, 2012, pp. 2139-2146, vol. 100, No. 8.
De Rosa et al., "PLGA Microspheres Encapsulating siRNA", RNA Interference: Challenges and Therapeutic Opportunities, Methods in Molecular Biology, 2015, pp. 43-51, vol. 1218, Springer Science+Business Media, New York.
De Visscher et al., "Improved endothelialization and reduced thrombosis by coating a synthetic vascular graft with fibronectin and stem cell homing factor sdf-1α", Acta Biomaterialia, 2012, pp. 1330-1338, vol. 8.
Desai et al., "Role of prosthetic conduits in coronary artery bypass grafting", European Journal of Cardio-Thoracic Surgery, 2011, pp. 394-398, vol. 40.
Diwan et al., "Pegylation enhances protein stability during encapsulation in PLGA microspheres", Journal of Controlled Release, 2001, pp. 233-244, vol. 73.
Dokken, "The Pathophysiology of Cardiovascular Disease and Diabetes: Beyond Blood Pressure and Lipids", Diabetes Spectrum, 2008, pp. 160-165, vol. 21, No. 3.
Duncan et al., "TGFβR1 Inhibition Blocks the Formation of Stenosis in Tissue-Engineered Vascular Grafts", Journal of the American College of Cardiology, 2015, pp. 512-514, vol. 65, No. 5.
Eghtesad et al., "Effect of rapamycin on immunity induced by vector-mediated dystrophin expression in mdx skeletal muscle", Scientific Reports, 2012, 6 pages, vol. 2, Article No. 399.
Elisseeff et al., "Controlled-release of IGF-I and TGF-β1 in a photopolymerizing hydrogel for cartilage tissue engineering", Journal of Orthopaedic Research, 2001, pp. 1098-1104, vol. 19.
El-Kurdi et al., "Transient elastic support for vein grafts using a constricting microfibrillar polymer wrap" Biomaterials, 2008, pp. 3213-3220, vol. 29.
Gauvin et al., "A Novel Single-Step Self-Assembly Approach for the Fabrication of Tissue-Engineered Vascular Constructs", Tissue Engineering: Part A, 2010, pp. 1737-1747, vol. 16, No. 5.
Gerthoffer, "Mechanisms of Vascular Smooth Muscle Cell Migration", Circulation Research, 2007, pp. 607-621, vol. 100, No. 5.
Gnecchi et al., "Paracrine Mechanisms in Adult Stem Cell Signaling and Therapy", Circulation Research, 2008, pp. 1204-1219, vol. 103, No. 11.
Grosskreutz et al., "Vascular Endothelial Growth Factor-Induced Migration of Vascular Smooth Muscle Cells in Vitro", Microvascular Research, 1999, pp. 128-136, vol. 58.
Grundmann et al., "Arteriogenesis: basic mechanisms and therapeutic stimulation", European Journal of Clinical Investigation, 2007, pp. 755-766, vol. 37.

(56) References Cited

OTHER PUBLICATIONS

Guan et al., "Biodegradable poly (ether ester urethane) urea elastomers based on poly (ether ester) triblock copolymers and putrescine: synthesis, characterization and cytocompatibility", Biomaterials, 2004, pp. 85-96, vol. 25.
Guan et al., "Preparation and characterization of highly porous, biodegradable polyurethane scaffolds for soft tissue applications", Biomaterials, 2005, pp. 3961-3971, vol. 26.
Guan et al., "Synthesis, Characterization and Cytocompatibility of Polyurethaneurea Elastomers with Designed Elastase Sensitivity", Biomacromolecules, 2005, pp. 2833-2842, vol. 6.
Hao et al., "Short Telomeres, even in the Presence of Telomerase, Limit Tissue Renewal Capacity", Cell, 2005, pp. 1121-1131, vol. 123.
Hashi et al., "Antithrombogenic property of bone marrow mesenchymal stem cells in nanofibrous vascular grafts", Proceedings of the National Academy of Sciences of the U.S A., 2007, pp. 11915-11920, vol. 104, No. 29.
He et al., "Newly Designed Compliant Hierarchic Hybrid Vascular Graft Wrapped With Microprocessed Elastomeric Film-II: Morphogenesis and Compliance Change Upon Implantation", Cell Transplantation, 2002, pp. 75-87, vol. 11.
He et al., "Canine endothelial progenitor cell-lined hybrid vascular graft with nonthrombogenic potential", Journal of Thoracic and Cardiovascular Surgery, 2003, pp. 455-464, vol. 126, No. 2.
He et al., "Preliminary In-Vivo Assessment of Adult Human Stem Cell-Based Tissue-Engineered Vascular Graft", Annual Fall Meeting of the Biomedical Engineering Society, 2009.
He et al., "Pericyte-based human tissue engineered vascular grafts", Biomaterials, 2010, pp. 8235-8244, vol. 31.
He et al., "Rapid Engineered Small Diameter Vascular Grafts from Smooth Muscle Cells", Cardiovascular Engineering and Technology, 2011, pp. 149-159, vol. 2, No. 3.
Hibino et al., "The tissue-engineered vascular graft using bone marrow without culture", The Journal of Thoracic and Cardiovascular Surgery, 2005, pp. 1064-1070, vol. 129.
Hibino et al., "Late-term results of tissue-engineered vascular grafts in humans", The Journal of Thoracic and Cardiovascular Surgery, 2010, pp. 431-436, vol. 139, No. 2.
Hibino et al., "Comparison of Human Bone Marrow Mononuclear Cell Isolation Methods for Creating Tissue-Engineered Vascular Grafts: Novel Filter System Versus Traditional Density Centrifugation Method", Tissue Engineering: Part C, 2011, pp. 993-998, vol. 17, No. 10.
Soletti et al., "In vivo performance of a phospholipid-coated bioerodable elastomeric graft for small-diameter vascular applications", Journal of Biomedical Materials Research Part A, 2011, pp. 436-448, vol. 96.
Stacy et al., "Targeted imaging of matrix metalloproteinase activity in the evaluation of remodeling tissue-engineered vascular grafts implanted in a growing lamb model", The Journal of Thoracic and Cardiovascular Surgery, 2014, pp. 2227-2233, vol. 148.
Stankus et al., "Microintegrating smooth muscle cells into a biodegradable, elastomeric fiber matrix", Biomaterials, 2006, pp. 735-744, vol. 27.
Stankus et al., "Fabrication of cell microintegrated blood vessel constructs through electrohydrodynamic atomization", Biomaterials, 2007, pp. 2738-2746, vol. 28.
Stolzing et al., "Diabetes Induced Changes in Rat Mesenchymal Stem Cells", Cells Tissues Organs, 2010, pp. 453-465, vol. 191.
Sun et al., "Sustained Release of Multiple Growth Factors from Injectable Polymeric System as a Novel Therapeutic Approach Towards Angiogenesis", Pharmaceutical Research, 2010, pp. 264-271, vol. 27, No. 2.
Tara et al., "Well-organized neointima of large-pore poly (l-lactic acid) vascular graft coated with poly (l-lactic-co-ε-caprolactone) prevents calcific deposition compared to small-pore electrospun poly (l-lactic acid) graft in a mouse aortic implantation model", Atherosclerosis, 2014, pp. 684-691, vol. 237.

Tara et al., "Evaluation of remodeling process in small-diameter cell-free tissue-engineered arterial graft", Journal of Vascular Surgery, 2015, pp. 734-743, vol. 62.
Tengood et al.,"Sequential delivery of vascular endothelial growth factor and sphingosine 1-phosphate for angiogenesis", Biomaterials, 2010, pp. 7805-7812, vol. 31.
Tengood et al.,"Sequential Delivery of Basic Fibroblast Growth Factor and Platelet-Derived Growth Factor for Angiogenesis", Tissue Engineering: Part A, 2011, pp. 1181-1189, vol. 17, Nos. 9 and 10.
Torikai et al.,"A self-renewing, tissue-engineered vascular graft for arterial reconstruction", The Journal of Thoracic and Cardiovascular Surgery, 2008, pp. 37-45, vol. 136, No. 1.
Udelsman et al.,"Characterization of evolving biomechanical properties of tissue engineered vascular grafts in the arterial circulation", Journal of Biomechanics, 2014, pp. 2070-2079, vol. 47.
Walker, "The Bicinchoninic Acid (BCA) Assay for Protein Quantitation", Methods in Molecular Biology, vol. 32: Basic Protein and Peptide Protocols, 1994, pp. 5-8, Humana Press Inc., Totowa, New Jersey.
Wang et al.,"Growth factor gradients via microsphere delivery in biopolymer scaffolds for osteochondral tissue engineering", Journal of Controlled Release, 2009, pp. 81-90, vol. 134.
Watanabe et al.,"Tissue-Engineered Vascular Autograft: Inferior Vena Cava Replacement in a Dog Model", Tissue Engineering, 2001, pp. 429-439, vol. 7, No. 4.
Weinbaum et al.,"Deficiency in Microfibril-associated Glycoprotein-1 Leads to Complex Phenotypes in Multiple Organ Systems", The Journal of Biological Chemistry, 2008, pp. 25533-25543, vol. 283, No. 37.
Weinbaum et al.,"Monitoring Collagen Transcription by Vascular Smooth Muscle Cells in Fibrin-Based Tissue Constructs", Tissue Engineering: Part C, 2010, pp. 459-467, vol. 16, No. 3.
Weinbaum et al.,"The Matrix-Binding Domain of Microfibril-Associated Glycoprotein-1 Targets Active Connective Tissue Growth Factor to a Fibroblast-Produced Extracellular Matrix", Macromolecular Bioscience, 2010, pp. 1338-1344, vol. 10.
Weintraub et al.,"Frequency of Repeat Coronary Bypass or Coronary Angioplasty After Coronary Artery Bypass Surgery Using Saphenous Venous Grafts", The American Journal of Cardiology, 1994, pp. 103-112, vol. 73, No. 2.
Williams et al.,"Adipose Stromal Vascular Fraction Cells Isolated Using an Automated Point of Care System Improve the Patency of Expanded Polytetrafluoroethylene Vascular Grafts", Tissue Engineering: Part A, 2013, pp. 1295-1302, vol. 19, Nos. 11 and 12.
Wu et al.,"Fast-degrading elastomer enables rapid remodeling of a cell-free synthetic graft into a neoartery", Nature Medicine, 2012, pp. 1148-1154, vol. 18, No. 7.
Xu et al.,"Controlled dual release of hydrophobic and hydrophilic drugs from electrospun poly (l-lactic acid) fiber mats loaded with chitosan microspheres", Materials Letters, 2011, pp. 2800-2803, vol. 65.
Yokota et al.,"In situ tissue regeneration using a novel tissue-engineered, small-caliber vascular graft without cell seeding", The Journal of Thoracic and Cardiovascular Surgery, 2008, pp. 900-907, vol. 136.
Yu et al.,"The effect of stromal cell-derived factor-1α/heparin coating of biodegradable vascular grafts on the recruitment of both endothelial and smooth muscle progenitor cells for accelerated regeneration", Biomaterials, 2012, pp. 8062-8074, vol. 33.
Zeng et al.,"The promotion of endothelial progenitor cells recruitment by nerve growth factors in tissue-engineered blood vessels", Biomaterials, 2010, pp. 1636-1645, vol. 31.
Zeng et al.,"The use of BDNF to enhance the patency rate of small-diameter tissue-engineered blood vessels through stem cell homing mechanisms", Biomaterials, 2012, pp. 473-484, vol. 33.
Zhang et al.,"A Novel Small-Diameter Vascular Graft: In Vivo Behavior of Biodegradable Three-Layered Tubular Scaffolds", Biotechnology and Bioengineering, 2008, pp. 1007-1015, vol. 99, No. 4.
Zhao et al.,"A Novel Strategy to Engineer Small-Diameter Vascular Grafts From Marrow-Derived Mesenchymal Stem Cells", Artificial Organs, 2012, pp. 93-101, vol. 36, No. 1.

(56) References Cited

OTHER PUBLICATIONS

Zhao et al.,"The development of a tissue-engineered artery using decellularized scaffold and autologous ovine mesenchymal stem cells", Biomaterials, 2010, pp. 296-307, vol. 31.
Zhou et al.,"Beneficial effects of granulocyte-colony stimulating factor on small-diameter heparin immobilized decellularized vascular graft", Journal of Biomedical Materials Research Part A, 2010, pp. 600-610, vol. 95, No. 2.
Zhu et al.,"Development of anti-atherosclerotic tissue-engineered blood vessel by A20-regulated endothelial progenitor cells seeding decellularized vascular matrix", Biomaterials, 2008, pp. 2628-2636, vol. 29.
Zhu et al.,"The effect of age on osteogenic, adipogenic and proliferative potential of female adipose-derived stem cells", Journal of Tissue Engineering and Regenerative Medicine, 2009, pp. 290-301, vol. 3.
Zimmerlin et al.,"Regenerative Therapy and Cancer: In Vitro and In Vivo Studies of the Interaction Between Adipose-Derived Stem Cells and Breast Cancer Cells from Clinical Isolates", Tissue Engineering: Part A, 2011, pp. 93-106, vol. 17, Nos. 1 and 2.
Hibino et al., "Tissue-engineered vascular grafts form neovessels that arise from regeneration of the adjacent blood vessel", The FASEB Journal, 2011, pp. 2731-2739, vol. 25, No. 8.
Hibino et al., "A critical role for macrophages in neovessel formation and the development of stenosis in tissue-engineered vascular grafts", The FASEB Journal, 2011, pp. 4253-4263, vol. 25, No. 12.
Hibino et al., "Evaluation of the use of an induced puripotent stem cell sheet for the construction of tissue-engineered vascular grafts", The Journal of Thoracic Cardiovascular Surgery, 2012, pp. 696-703, vol. 143, No. 3.
Hibino et al., "The innate immune system contributes to tissue-engineered vascular graft performance", The FASEB Journal, 2011, pp. 2431-2438, vol. 29, No. 6.
Hiyama et al., "Telomere and telomerase in stem cells", British Journal of Cancer, 2007, pp. 1020-1024, vol. 96.
Hjortnaes et al., "Intravital Molecular Imaging of Small-Diameter Tissue-Engineered Vascular Grafts in Mice: A Feasibility Study", Tissue Engineering: Part C, 2010, pp. 597-607, vol. 16, No. 4.
Hoerstrup et al., "Functional Growth in Tissue-Engineered Living, Vascular Grafts Follow-Up at 100 Weeks in a Large Animal Model", Circulation, 2006, pp. I-159-166,vol. 114.
Hong et al., "A small diameter, fibrous vascular conduit generated from a poly(ester urethane)urea and phospholipid polymer blend", Biomaterials, 2009, pp. 2457-2467, vol. 30.
Hsu et al., "The Incidence of End-Stage Renal Disease Is Increasing Faster than the Prevalence of Chronic Renal Insufficiency", Annals of Internal Medicine, 2004, pp. 95-101, vol. 141.
Isenberg et al., "Small-Diameter Artificial Arteries Engineered In Vitro", Circulation Research, 2006, pp. 25-35, vol. 98.
Janairo et al., "Heparin-Modified Small-Diameter Nanofibrous Vascular Grafts", IEEE Transactions on Nanobioscience, 2012, pp. 22-27, vol. 11, No. 1.
Janairo et al., "Mucin Covalently Bonded to Microfibers Improves the Patency of Vascular Grafts", Tissue Engineering: Part A, 2014, pp. 285-293, vol. 20, Nos. 1 and 2.
Jay et al., "Dual delivery of VEGF and MCP-1 to support endothelial cell transplantation for therapeutic vascularization", Biomaterials, 2010, pp. 3054-3062, vol. 31.
Jhunjhunwala et al., "Delivery of rapamycin to dendritic cells using degradable microparticles", Journal of Controlled Release, 2009, pp. 191-197, vol. 133.
Jhunjhunwala et al., "Controlled release formulations of IL-2, TGF-β1 and rapamycin for the induction of regulatory T cells", Journal of Controlled Release, 2012, pp. 78-84, vol. 159.
Jönsson et al., "Circulating particles during cardiac surgery", Interactive Cardiovascular and Thoracic Surgery, 2009, pp. 538-542, vol. 8.
Josowitz et al., "Characterizing the Seeding Distribution of Microspheres in Tissue Engineered Vascular Grafts", 2015 BMES Annual Meeting, 2015, 1 page.

Kamalasanan et al., "Patchy, Anisotropic Microspheres with Soft Protein Islets", Angewandte Chemie International Ed. English, 2011, pp. 8706-8708, vol. 123.
Kaushal et al., "Functional small-diameter neovessels created using endothelial progenitor cells expanded ex vivo", Nature Medicine, 2001, pp. 1035-1040, vol. 7, No. 9.
Kawai et al., "Accelerated tissue regeneration through incorporation of basic fibroblast growth factor-impregnated gelatin microspheres into artificial dermis", Biomaterials, 2000, pp. 489-499, vol. 21.
Keats et al., "Vascular stem cells in diabetic complications: evidence for a role in the pathogenesis and the therapeutic promise", Cardiovascular Diabetology, 2012, 10 pages, vol. 11, No. 37.
Kelm et al., "Functionality, growth and accelerated aging of tissue engineered living autologous vascular grafts", Biomaterials, 2012, pp. 8277-8285, vol. 33.
Khosravi et al., "Biomechanical Diversity Despite Mechanobiological Stability in Tissue Engineered Vascular Grafts Two Years Post-Implantation", Tissue Engineering: Part A, 2015, pp. 1529-1538, vol. 21, Nos. 9 and 10.
Kim et al., "Porous chitosan scaffold containing microspheres loaded with transforming growth factor-β1: Implications for cartilage tissue engineering", Journal of Controlled Release, 2003, pp. 365-374, vol. 91.
Kinnaird et al., "Marrow-Derived Stromal Cells Express Genes Encoding a Broad Spectrum of Arteriogenic Cytokines and Promote In Vitro and In Vivo Arteriogenesis Through Paracrine Mechanisms", Circulation Research, 2004, pp. 678-685, vol. 94.
Klinkert et al., "Saphenous Vein Versus PTFE for Above-Knee Femoropopliteal Bypass. A Review of the Literature", European Journal of Vascular and Endovascular Surgery, 2004, pp. 357-362, vol. 27.
Koch et al., "Fibrin-polylactide-based tissue-engineered vascular graft in the arterial circulation", Biomaterials, 2010, pp. 4731-4739, vol. 31.
Kohler et al., "Dialysis access failure: A sheep model of rapid stenosis", Journal of Vascular Surgery, 1999, pp. 744-751, vol. 30, No. 4.
Kokai et al., "Protein bioactivity and polymer orientation is affected by stabilizer incorporation for double-walled microspheres", Journal of Controlled Release, 2010, pp. 168-176, vol. 141.
Konig et al., "Mechanical properties of completely autologous human tissue engineered blood vessels compared to human saphenous vein and mammary artery", Biomaterials, 2009, pp. 1542-1550, vol. 30.
Krawiec et al., "Adult stem cell-based tissue engineered blood vessels: A review", Biomaterials, 2012, pp. 3388-3400, vol. 33.
Krawiec et al., "Functional Stem-Cell Based Tissue Engineered Vascular Grafts for High-Risk Donor Populations", Dissertation, 2015, University of Pittsburgh, Pittsburgh, PA.
Krawiec et al., "A Cautionary Tale for Autologous Vascular Tissue Engineering: Impact of Human Demographics on the Ability of Adipose-Derived Mesenchymal Stem Cells to Recruit and Differentiate into Smooth Muscle Cells", Tissue Engineering: Part A, 2015, pp. 1529-1538, vol. 21, Nos. 9 and 10.
Krawiec et al., "Adipose-Derived Stem Cells from Diabetic Donors is Associated with Thrombotic Failure of Autologous Tissue Engineered Vascular Grafts due to Impaired Fibrinolytic Activity", North American Vascular Biology Organization (NAVBO)—Vascular Biology 2015, 2015, 1 page.
Krawiec et al., "Adipose-Derived Stem Cells from Diabetic Donors is Associated with Thrombotic Failure of Autologous Tissue Engineered Blood Vessels", Summer Biomechanics, Bioengineering and Blotransport Conference, Jun. 17-20, 2015, Utah.
Krawiec et al., "In Vivo Functional Evaluation of Tissue-Engineered Vascular Grafts Fabricated Using Human Adipose-Derived Stem Cells from High Cardiovascular Risk Populations", Tissue Engineering: Part A, 2016, pp. 765-775, vol. 22, Nos. 9 and 10.
Kurobe et al., "Development of Small Diameter Nanofiber Tissue Engineered Arterial Grafts", PLoS ONE, 2015, vol. 10, No. 4, Article e0120328.
L'Heureux et al., "A completely biological tissue-engineered human blood vessel", FASEB Journal, 1998, pp. 47-56, vol. 12.

(56) References Cited

OTHER PUBLICATIONS

L'Heureux et al., "Human tissue-engineered blood vessels for adult arterial revascularization", 2006, Nature Medicine, pp. 361-365, vol. 12, No. 3.

L'Heureux et al., "Technology Insight: The evolution of tissue-engineered vascular grafts—from research to clinical practice", Nature Clinical Practice Cardiovascular Medicine, 2007, pp. 389-395, vol. 4, No. 7.

L'Heureux et al., "Tissue-Engineered Blood Vessel for Adult Arterial Revascularization", The New England Journal of Medicine, 2007, pp. 1451-1453, vol. 357, No. 14.

Lavasani et al., "Muscle-derived stem/progenitor cell dysfunction limits healthspan and lifespan in a murine progeria model", Nature Communications, 2012, 12 pages, vol. 3, No. 608.

Lawson et al., "VS5 Human Tissue-Engineered Grafts for Hemodialysis: Development, Preclinical Data, and Early Investigational Human Implant Experience", Journal of Vascular Surgery, 2014, pp. 32S-33S, vol. 59, No. 6S.

Lee et al., "Nanofiber alignment and direction of mechanical strain affect the ECM production of human ACL fibroblast", Biomaterials, 2005, pp. 1261-1270, vol. 26.

Lee et al., "Human progenitor cell recruitment via sdf-1α coacervate-laden pgs vascular grafts", Biomaterials, 2013, pp. 9877-9885, vol. 34.

Lee et al., "Polydopamine-mediated immobilization of multiple bioactive molecules for the development of functional vascular graft materials", Biomaterials, 2012, pp. 8343-8352, vol. 33.

Lepidi et al., "Hyaluronan Biodegradable Scaffold for Small-caliber Artery Grafting: Preliminary Results in an Animal Model", European Journal of Vascular and Endovascular Surgery, 2006, pp. 411-417, vol. 32.

Liang et al., "Dual release of dexamethasone and tgf-β3 from polymeric microspheres for stem cell matrix accumulation in a rat disc degeneration model", Acta Biomaterialia, 2013, pp. 9423-9433, vol. 9.

Lim et al., "Tissue-Engineered Blood Vessels With Endothelial Nitric Oxide Synthase Activity", Journal of Biomedical Materials Research Part B Applied Biomaterials, 2008, pp. 537-546, vol. 85, No. 2.

Liu et al., "Functional tissue-engineered blood vessels from bone marrow progenitor cells", Cardiovascular Research, 2007, pp. 618-628, vol. 75.

\* cited by examiner

ARTIFICIAL CELLS AND DELIVERY DEVICES FOR USE IN TISSUE ENGINEERING, AND RELATED METHODS

CROSS REFERENCE TO RELATED APPLICATIONS

This application is the United Sates national phase of International Application No. PCT/US2017/039973 filed Jun. 29, 2017, and claims the benefit of U.S. Provisional Patent Application No. 62/356,754, filed Jun. 30, 2016, each of which is incorporated herein by reference in its entirety.

Controlled-release devices, such as particles, are provided, comprising conditioned media for use in tissue engineering. Methods of making and using the devices or particles are also provided.

Cardiovascular disease is the leading cause of death within the US, and approximately 600,000 surgical procedures that utilize revascularization techniques, such as bypass grafting, are performed annually. The current clinical standard conduit for small diameter (<6 mm) arterial bypass grafting is the human saphenous vein, but these are often unavailable or damaged. Also, 30% of patients who undergo coronary artery bypass procedures with saphenous veins need re-operation within 12 years due to occlusion of the graft by neointimal hyperplasia or accelerated atherosclerosis. Unmodified and non-degradable synthetic grafts are limited in their lack of growth and remodeling potential and their preponderance to thrombotic complications. However, biodegradable materials which act as a scaffold for regeneration of a "living" graft via replacement with host tissue are often used in vascular tissue engineering applications. These tissue engineered vascular grafts (TEVGs) have great clinical promise as they may offer substantial benefit in reducing intimal hyperplasia and thrombosis, and allow tissue growth and remodeling.

In-vivo testing of stem cell-based small-diameter tissue engineered vascular grafts (TEVGs) has shown that they have great clinical promise Grafts that are currently used in cardiac and lower extremity revascularization procedures or as arteriovenous (AV) access grafts for dialysis are not ideal and have significant failure rates.

There is therefore a need for effective tissue growth scaffolds, both in vascular engineering and, more generally, in tissue engineering for any application. There is also a need for drug delivery devices that release encapsulated factors in a therapeutically-effective manner, that is as a cell would.

SUMMARY

According to one aspect of the invention, a composition is provided comprising a first particle comprising conditioned medium from a cell culture within the particle, and having a first release profile of the conditioned medium, optionally in blood, water, PBS or saline.

According to another aspect of the invention a tissue growth scaffold comprising a porous material of a biocompatible polymer and a composition comprising a first particle comprising conditioned medium from a cell culture within the particle, and having a first release profile of the conditioned medium, optionally in blood, water, PBS or saline.

In another aspect of the invention, a blood vessel growth scaffold is provided comprising a porous tube of a biocompatible polymer and a composition comprising a first particle comprising conditioned medium from a cell culture within the particle, and having a first release profile of the conditioned medium, optionally in blood, water, PBS or saline.

According to a further aspect of the invention a method of making a tissue growth scaffold is provided. The method comprises distributing a composition comprising a first particle comprising conditioned medium from a cell culture within the particle, and having a first release profile of the conditioned medium, optionally in blood, water, PBS or saline in a biocompatible polymer.

According to yet another aspect of the invention, a controlled release pharmaceutical device comprising conditioned medium is provided.

In another aspect of the invention, a method of preparing a controlled-release composition is provided, comprising: culturing cells in cell culture medium, optionally for at least one hour, for example, from one hour to two weeks, including increments therebetween, such as: 1, 2, 3, 6, 8, 12, 18, or 24 hours, 1, 2, 3, 4, 5, 6, 7, 8, 9, 10, 11, 12, 13, or 14 days, and increments therebetween up to one week and 1-5 days and increments therebetween, thereby producing conditioned medium; collecting the conditioned medium; optionally concentrating the conditioned medium; emulsifying, for example by sonicating, the medium in a volatile solvent (e.g., an organic solvent having a boiling point less than 100° C., for example pentane, cyclopentane, hexane, cyclohexane, benzene, chloroform, diethyl ether, or dichloromethane), comprising a polymer to produce a micro-emulsion; and homogenizing the micro-emulsion in an aqueous phase, so that particles precipitate as the solvent evaporates.

In another aspect of the invention, a method of producing tissue, such as blood vessel, in vitro or in a patient, is provided, comprising implanting a tissue growth scaffold comprising a porous material of a biocompatible polymer and a composition comprising a first particle comprising conditioned medium from a cell culture within the particle, and having a first release profile of the conditioned medium, optionally in blood, water, PBS or saline, in a patient.

BRIEF DESCRIPTION OF THE DRAWINGS

In FIG. 8C, in reference to FIG. 4, we expect a family of "burst-release" particles to empty their payload by 2 days—six families are represented, each with a different shade arc. The effective sustained release is indicated with a horizontal dashed line. New families of artMSC will be needed until the point when MSC are no longer present, SMC have moved in, and a full endothelial layer has formed. In the hypothetical case depicted in this image, the two right-most arcs would not be needed, just the first four.

DETAILED DESCRIPTION

Figure 1:
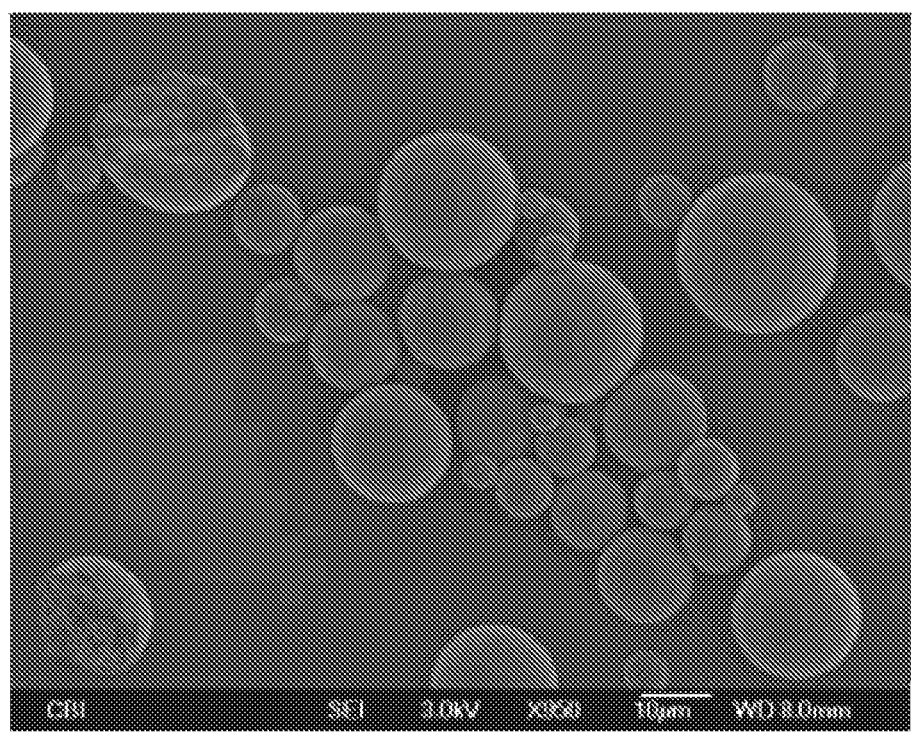
FIG. 1 shows scanning electron microscopy of 20 μm non-porous particles. These were fabricated according to the methods described.

Other than in the operating examples, or where otherwise indicated, the use of numerical values in the various ranges specified in this application are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps. For definitions provided herein, those definitions refer to word forms, cognates and grammatical variants of those words or phrases.

As used herein, the term "polymer composition" is a composition comprising one or more polymers. As a class, "polymers" includes, without limitation, homopolymers, heteropolymers, copolymers, block polymers, block co-polymers and can be both natural and synthetic. Homopolymers contain one type of building block, or monomer, whereas copolymers contain more than one type of monomer.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g. terminal groups, that are modified during polymerization are changed, removed, and/or relocated, and certain bonds may be added, removed, and/or modified. An incorporated monomer is referred to as a "residue" of that monomer. A polymer is said to comprise a specific type of linkage if that linkage is present in the polymer. Unless otherwise specified, molecular weight for polymer compositions refers to weight average molecular weight (Mw). A "moiety" is a portion of a molecule, compound or composition, and includes a residue or group of residues within a larger polymer.

A bioerodible polymer is a polymer that degrades in vivo over a time period, which can be tailored to erode over a time period ranging from days to months, and up to two years, for example a polymeric structure, when placed in vivo, will fully degrade within a time period of up to two years. By "bioerodible," it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters, anhydrides, or polyanhydrides, which can be useful in, for example and without limitation, controlling the degradation rate of the scaffold or particles and/or the release rate of therapeutic agents, such as the conditioned medium, from the scaffold or particles.

By "biocompatible," it is meant that a polymer composition and its normal degradation in vivo products are cytocompatible and are substantially non-toxic and non-carcinogenic in a patient within useful; practical and/or acceptable tolerances. By "cytocompatible," it is meant that the polymer can sustain a population of cells and/or the polymer composition, device, and degradation products thereof are not cytotoxic and/or carcinogenic within useful, practical and/or acceptable tolerances. For example, the polymer when placed in a human epithelial cell culture does not adversely affect the viability, growth, adhesion, and number of cells. In one non-limiting embodiment, the compositions and/or devices are "biocompatible" to the extent they are acceptable for use in a human or veterinary patient according to applicable regulatory standards in a given jurisdiction. In another example the biocompatible polymer, when implanted in a patient, does not cause a substantial adverse reaction or substantial harm to cells and tissues in the body, for instance, the polymer composition or device does not cause unacceptable inflammation, necrosis, or an infection resulting in harm to tissues from the implanted scaffold. A "patient" is a human or non-human animal.

Non-limiting examples of a bioreodible polymer useful for tissue or vascular growth scaffolds or the described particles described herein include: a polyester, a polyester-containing copolymer, a polyanhydride, a polyanhydride-containing copolymer, a polyorthoester, and a polyorthoester-containing copolymer. In one aspect, the polyester or polyester-containing copolymer is a polylactic-co-glycolic) acid (PLGA) copolymer. In another embodiment, the bio-erodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid; poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).

Non-erodable polymers either do not erode substantially in vivo or erode over a time period of greater than two years. Compositions such as, for example and without limitation, PTFE, polyethylene-co-vinyl acetate), poly(n-butylmethacrylate), poly(styrene-b-isobutylene-b-styrene) and polyethylene terephthalate are considered to be non-erodable polymers. Other suitable non-erodable polymer compositions are broadly known in the art, for example in stent coating and transdermal reservoir technologies. The growth scaffolds described herein may comprise a non-erodible polymer composition.

Methods of preparation of the polymeric compositions described herein are broadly-known. For example, diamines and diols are useful building blocks for preparing the described polymer compositions. Diamines as described above have the structure $H_2N-R-NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as polycaprolactone-PEG copolymers, including polycaprolactone-b-polyethylene glycol-b-polycaprolactone triblock copolymers of varying sizes. Other building blocks for useful diols include, without limitation glycolides (e.g. polyglycolic acid (PGA)), lactides, dioxanones, and trimethylene carbonates. Diisocyanates have the general structure $OCN-R-NCO$, where "R" is an aliphatic or aromatic hydrocarbon or a hydrocarbon comprising aromatic and aliphatic regions. The hydrocarbon may be linear or branched.

As a class, stem cells and progenitor cells are cells that are capable of differentiation into another cell type, such as another progenitor cell or a fully differentiated, mature cell, for example and without limitation, a somatic cell, that has characteristic morphology and specialized functions. Stem cells are found in all multi-cellular organisms. Through mitotic cell division, they have the capacity to self-renew and can differentiate into a diverse range of specialized cell types. Mammalian stem cells include as a class: embryonic stem cells, adult stem cells, and cord blood stem cells. Embryonic Stem cells are derived from the inner cell mass of pre-implantation embryos. Adult stem cells are found in adult tissue. Cord blood stem cells are derived from the umbilical cord, which is rich in hematopoietic stem cells—stem cells that can differentiate to form all cellular components of blood. Embryonic Stem cells are pluripotent. They are able to differentiate into all of the somatic cell types of the three primary germ layers: the ectoderm; the mesoderm and the endoderm. Embryonic Stem cells differentiate into the different cell types in the adult body. Absent stimulation to differentiate, embryonic Stem cells can expand indefinitely, maintaining pluripotency.

Adult stem cells also can self-renew indefinitely; however, unlike embryonic stem cells, are not pluripotent. They are multipotent in that they can differentiate into some, but not all mature cell types that have characteristic morphologies and specialized functions. Recent studies have shown that adult stem cells have a degree of plasticity and can be encouraged to differentiate into other cell lineages, a process also known as transdifferentiation. A non-exhaustive and non-limiting list of adult stem cells includes: mammary, intestinal, mesenchymal, endothelial, neural, olfactory, neural crest and testicular stem cells (adult germline stem cells. Exceptions to the lack of pluripotency of adult stem cells include non-embryonic cell types known as "Blastomere Like Stem Cells" (BLSCs) and "very small embryonic like" (VSEL) stem cells, which, though dormant, exhibit pluripotency (See, e.g., WO 2007100845).

Typically, stem cells generate an intermediate cell type or types before they achieve their fully differentiated state. The intermediate cell is called a precursor or progenitor cell. Progenitor or precursor cells in fetal or adult tissues are partly differentiated cells that divide and give rise to differentiated cells. Such cells are usually regarded as "committed" to differentiating into one or more further differentiated cell types along a particular cellular development pathway, but there are exceptions. Although they can differentiate into one or more cell types, unlike adult stem cells, adult progenitor cells cannot renew indefinitely, though they typically can retain their multipotency for several rounds of cell division.

Mesenchymal stem cells ("MSCs", also referred to as bone marrow stromal stem cells, skeletal stem cells, or mesenchymal stromal cells) are broadly-known, and make up a small proportion of the stromal cell population in the bone marrow. MSCs can generate bone, cartilage, and fat cells that support the formation of blood and fibrous connective tissue. They have been reported to be present in many tissues. Those from bone marrow (bone marrow stromal stem cells, skeletal stem cells) give rise to a variety of cell types: bone cells (osteoblasts and osteocytes), cartilage cells (chondrocytes), fat cells (adipocytes), and stromal cells that support blood formation. A variety of methods of preparing MSCs are known to those of skill in the art, e.g. as shown below.

For use in the methods, compositions and products described herein, the cells cultured for use in the production of conditioned are healthy, in that the cells are obtained from a healthy, non-aged human (or in the case of veterinary uses, from a healthy, non-aged animal), e.g., in the case of humans, a non-diabetic, non-aged (e.g., under 45 years old) person.

Cell growth media or medium is a solution used to support growth and optionally expansion of a cell population in vitro. A large variety of media are available commercially. Often serum, such as fetal bovine serum, is used to promote cell growth. Additional factors, including buffers, co-factors, antimicrobials, salts, cellular extracts and/or amino acids, carbon source(s), among other factors, are included in various media. For different mammalian cell types, different ingredients are present in any given medium, which often is optimized to promote growth and expansion of that given cell type. The end-use of the cells also is taken into consideration when formulating and optimizing a particular medium. For example, to produce cells or conditioned medium for use in human patients, "xeno free" (xenogeneic-free) media may be used, which contains no natural products, e.g., proteins or other potentially antigenic substances, obtained from non-human sources, such as fetal bovine serum, or cell extracts. "Xeno-free" relates to the species in which the conditioned media is to be used, and therefore if the conditioned media is to be used in humans or for propagating human cells, the media contains no non-human products (e.g. proteins or serum), while if the conditioned media is to be used for veterinary purposes, e.g. in dogs or for propagating dog cells, the media contains no products from a different species. A non-limiting example of a useful, xeno-free, medium for expansion of human mesenchymal stem cells is StemXVivo® Xeno-Free Human MSC Expansion Media (R&D Systems). Other media for expansion of mesenchymal stem cells are commercially available and/or described in the literature.

As indicated above, despite their clear value in the remodeling process and host acceptance of an implanted graft, the mesenchymal stem cells (MSCs) of an MSC-based TEVG are in fact a significant rate-limiting barrier to this technology reaching its clinical promise.

First, approaches to date have utilized cells from healthy humans or animals providing minimal relevance to realistic clinical situations—to patients at high cardiovascular risk who would routinely need this therapy. Autologous cell seeding of biodegradable scaffold materials is frequently utilized for TEVGs in order to offer resistance to acute thrombosis, to prevent stenosis, and to provide paracrine/secreted factors to encourage substantial remodeling of the graft in the form of host cell recruitment. Recent studies have shown that these seeded cells are not retained in the TEVGs long term but are needed acutely to provide these benefits until the host environment can adequately take over. Mesenchymal stem cells (MSCs) are a potent cell type which can lead to a successful TEVG, as they secrete pro-migratory, mitogenic, anti-thrombogenic, and immuno-regulatory proteins. However, the function of autologous cells is highly dependent on patient demographics. For example, studies have shown that MSCs from patient populations who would be routinely targeted by a vascular graft, including the elderly or diabetics, are functionally deficient, providing reduced ability to maintain TEVG patency, reduced anti-thrombotic activity, stunted differentiation, and lack of pro-migratory secreted factors, all which are counter to successful TEVG remodeling. As such, the promise of autologous MSCs in tissue engineering approaches for vascular replacement may not be tractable for those significant patient populations in need. Thus, pathological conditions that are present in high-risk patients, such as diabetics, have been shown to decrease the functionality of both their stem and vascular cells. TEVGs constructed with MSCs from diabetic patients exhibit lower patency rates than with MSCs from non-diabetic patients. This underscores the importance of finding alternative means to create effective TEVGs for these and other high-risk populations.

Second, cell-based TEVG approaches are also limited due to their failure to address practical barriers such as fabrication time and the need for in vitro or ex vivo cell or tissue culture. An approach requiring in vitro or ex vivo culture, for example, is clinically unrealistic due to excessive prep/wait time and costs. Regulatory concerns also arise with in vitro culture due to the potential for cellular transformation or contamination, particularly when the cells are exposed to animal-sourced media supplements (e.g., bovine serum).

While microsphere particles have been utilized to deliver distinct factors, the controlled delivery of MSC conditioned media within a tissue engineering application has yet to be achieved. Microspheres are commonly used as a delivery vehicle and offer the ability to fine tune their properties to achieve a variety of sizes (e.g., on the order of 1 µm and 10 µm) and timed release rates (e.g., <1 week and >1 month). Additionally, they have been extensively utilized to release several compounds ranging from growth factors (e.g., VEGF, FGF, PDGF, MCP-1, TGF-beta, EGF, BMP-2, BMP-7, IGF-1, drugs, peptides, and siRNAs). Often times these are delivered as single factors, but studies have begun to show the delivery of two factors simultaneously through encapsulation within either the same microsphere or using two separate populations. However, achieving therapeutically relevant doses and appropriately timed releases with microspheres has been difficult. Mixed results have been seen when encapsulating two different factors within the same formulation of particles either showing the same release profile or drastically different ones. Most often, investigators opt for approaches that utilize one microsphere encapsulated factor with another positioned externally in a separate medium or utilize different microsphere compositions when attempting to fine-tune temporal release.

Figure 3:
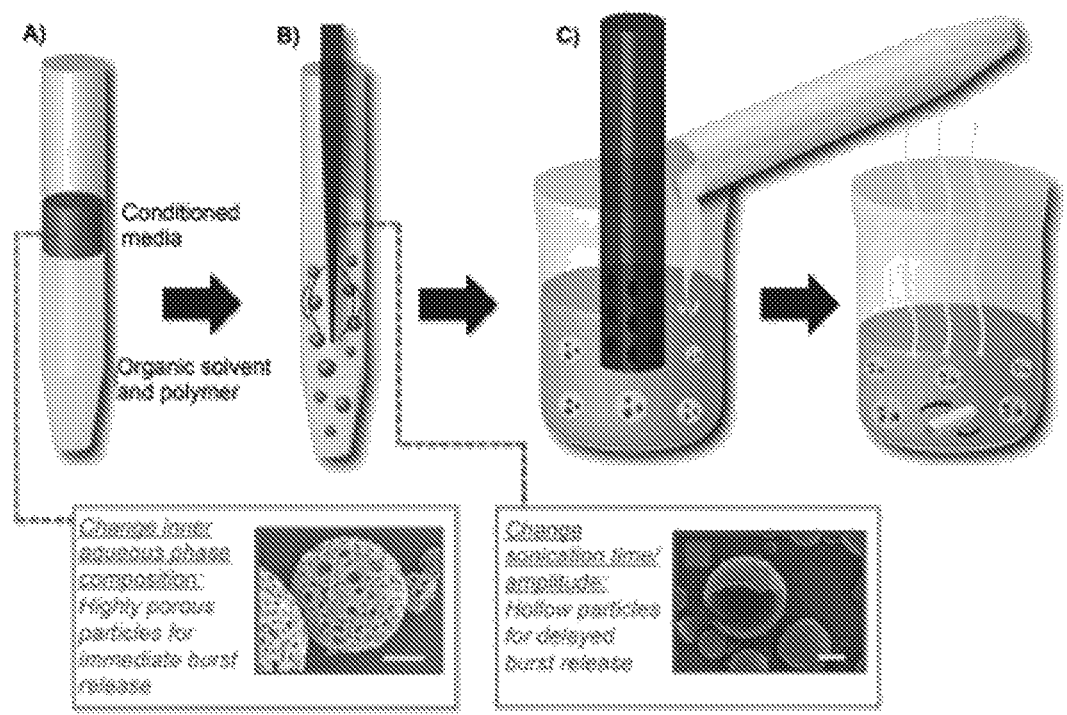
FIG. 3 is a scheme of particle fabrication. (Top) A schematic of the double-emulsion process outlined herein. Note that polymer molecular weight, polymer degradation rate, sonication power, and homogenization speed are all tailorable during fabrication. (Bottom) A table of the parameters that can be tuned in the computational model, as well as which factors are tailorable in the context of artMSC fabrication.

Polymer particles are tunable with regards to their release of cargo, which can be used to mimic the action of, e.g. MSCs in TEVG. Several parameters can be controllably varied for this purpose, including polymer composition, concentration and/or composition of encapsulated factors, and particle porosity (pore diameter) (Rothstein S N, Little S R. A "tool box" for rational design of degradable controlled release formulations. J Mater Chem 21, 29, 2011). Some of the fabrication methods that we use are highlighted in FIG. 3 and are presented in more detail in several publications (Rothstein S N, et al., A simple model framework for the prediction of controlled release from bulk eroding polymer matrices. J Mater Chem 18, 1873, 2008; Rothstein S N, et al., A unified mathematical model for the prediction of controlled release from surface and bulk eroding polymer matrices. Biomaterials 30, 1657, 2009; Rothstein S N, et al., A retrospective mathematical analysis of controlled release design and experimentation. Mol. Pharm. 9, 3003, 2012). A unique mathematical modeling techniques and finite element analysis (COMSOL Multiphysics) has been developed to directly translate desired release profiles into several physically relevant fabrication "instructions." This model uses five parameters as opposed to past models which require up to 19 ad hoc parameters, many of which cannot be measured and instead must be mathematically "fitted" for each system. The model's five design parameters can be easily tuned using fabrication machinery housed in our laboratories, including: 1) overall particle radius ($R_p$, which is experimentally governed by homogenization speed during a double emulsion fabrication process), 2) inner occlusion or pore size ($R_{ocs}$, controlled by sonication power input during the double emulsion process), 3) polymer molecular weight ($M_{wo}$, polymers of different $M_{wo}$'s are commercially available), 4) molecular weight of the drug/biomolecule ($M_{wd}$) and 5) the degradation rate constant for PLGA ($k_{Cw}$, exhaustively studied in the literature (Rothstein S N, et al. A simple model framework for the prediction of controlled release from bulk eroding polymer matrices. J Mater Chem 18, 1873, 2008; Rothstein S N, et al., A unified mathematical model for the prediction of controlled release from surface and bulk eroding polymer matrices. Biomaterials 30, 1657, 2009) for various, FDA-approved, PLGA copolymer residues) (FIG. 3). Together, these tunable formulation properties can predictably dictate the release behavior of a system and (in turn) the desired release profile can inform the engineer as to exactly how a formulation should be built in order to achieve that desired behavior. The in silica release profile can inform us how to make our particles without an extensive iterative experimental process (Rothstein S N, et al., A simple model framework for the prediction of controlled release from bulk eroding polymer matrices. J Mater Chem 18, 1873, 2008; Rothstein S N, et al., A unified mathematical model for the prediction of controlled release from surface and bulk eroding polymer matrices. Biomaterials 30, 1657, 2009; Rothstein S N, et al., A retrospective mathematical analysis of controlled release design and experimentation. Mol. Pharm, 9, 3003, 2012).

A cell free TEVG technology using artificial stem cells which do not possess the functional and practical limitations of autologous cell is therefore provided. Among the primary components of this system will be sets of novel, finely tuned particles that are engineered to locally and biomimetically release MSC secreted factors in a tissue engineered construct.

In one aspect of the invention, a drug product, device, drug dosage form, or, more generally a "product" is provided. Provided is a formulation of particles as a system for the controllable release of multiple bioactive factors produced by specific cell types, such as mesenchymal stem cells (MSCs). This is designed in such a way to mimic the secretion performed by the cells themselves. In one aspect, the formulation comprises particles or objects of any suitable degradable or non-degradable material, such as polymer, ceramic, or osmotic release systems, that are porous or non-porous, and conditioned media dispersed through the particle or object. Conditioned media, as described herein, may be delivered via any useful product, and in one aspect, the product comprises a delivery matrix comprising the conditioned media, for release of the conditioned media in a controlled manner. The matrix can be any useful composition or physical structure, e.g., as are known in the pharmaceutical arts. The matrix may have any suitable shape; such as a particle, for example, as described herein, or as fibers, sheets, capsules, or virtually any three-dimensional shape, with the conditioned media incorporated into or within (e.g., in pores, chambers, lumen, etc. within the matrix) the matrix. In terms of composition, the matrix may have any suitable composition and structure useful for delivery of the constituents of consistent media. In one aspect, the matrix is polymeric, e.g. as a porous and/or biodegradable matrix, ceramic, or lipid (e.g. as liposomes or micellular), as are broadly known in the pharmaceutical arts. As used herein, the term "ceramic composition" is a composition comprising ceramic, such as, without limitation: calcium phosphates, silica, alumina, zirconia and titanium dioxide; which are used for various medical applications due to their positive interactions with human tissues. Ceramic composites or compositions are characterized by high mechanical strength; good body-response, and low or non-existing biodegradability, Since degradability of ceramic comprising compounds is slow, porosity may be introduced. Ceramics may be combined with polymers, such as polylactic acid-based polymers, etc. This combination may be useful as it is combines the tailored degradability and high release efficiencies of the polymer with the delayed/sustained release characteristics of the ceramic material. In another aspect; the matrix may form an osmotic release system, wherein the drugs, growth factors, therapeutic agents; etc. are controllably released by osmosis. In one aspect; the conditioned media is lipid encapsulated, including, e.g.; triacylglycerides, phospholipids, waxes, or similar materials.

By "slow" release, "delayed" release, "extended" release, "modified"-release, it is meant that the constituents of the conditioned media are released from the matrix over time, and not immediately as a bolus, for example, and without limitation, over 1, 2, 3, 4, 5, 6, 7, 8, 9, 10, 11, 12, 18, or 24 hours, or over 1, 2, 3, 4, 5, 6, 7, 14, or 21 days, or even over weeks or months.

According to further aspects of the invention; particles, e.g. polymer particles are used as a matrix for pharmaceutically-acceptable delivery conditioned media. Particles can be of any useful size, typically ranging from nanometer to micrometer scale (that is from 1 nm up to 1 mm average diameter); though larger or smaller particles are possible. In one aspect, the particle or object comprises a polymer. The polymer can be any pharmaceutically-acceptable material, such as a polymer, such as a polylactic-co-glycolic acid) copolymer, that encapsulates MSC-conditioned media. In one aspect, particles are prepared by a unique fabrication scheme described herein that allows for secretion of multiple bioactive factors over an extended time course. Such particles are referred to herein as "artificial cells", "artificial stem cells" (relating specifically to stem cells) or "artificial MSCs" (relating specifically to MSCs). MSCs are exemplary, and the compositions, methods, and devices described herein are equally applicable to other cell types.

As used herein "particles" do not imply a size, though in one aspect the particles have a longest measurement of less than 1 mm, and in another, less than 100 µM. In one aspect the particles can pass through a mesh having the stated pore size. For example, a particle having a longest measurement of 100 µM can pass through a mesh having a pore size of 100 µM, but not a mesh having a smaller pore size. The particles may be any shape, such as spherical, oblong, irregular, etc., and therefore can be microspheres or nanospheres. The combination of delivered factors and the way in which they are delivered are unique features of the compositions, structures and devices provided herein. The method of delivery can be tuned to release individual factors for alternative applications, Under traditional fabrication methods for extended release particles, particles are created in non-porous or porous formulations. While this cumulatively achieves a sustained release, the diameter variation of different loaded factors may cause differences in release time due to size-exclusion and entrapment within the walls of these particles. To overcome this limitation according to one aspect of the invention, "artificial cells" or, e.g., "artificial MSCs" are fabricated utilizing highly-porous particles which perform an immediate bulk release of their cargo and achieve simultaneous release of multiple factors. For delivery over an extended time course, a population of "artificial cells" is provided comprising multiple subpopulations of particles—each tuned to release on a time-delay. Utilized together, this allows for a consistent stream of bolus releases which cumulatively achieving a sustained release over time. Achieving consistent release of multiple factors over an extended time course is a significant challenge in the field of drug delivery. Artificial cells, such as MSCs (e.g.), as described herein overcome this by their unique ability to deliver a multitude of factors simultaneously and do so consistently over time.

Additionally, as this acts to mimic the secretion of factors by cells, progenitor cells, stem cells, or MSCs, artificial cells can be utilized as an alternative to live cells to achieve the same benefits of real cells. This is beneficial in situations where there are immunological concerns (as in the case of allogeneic or xenogenic cell use) as particles will not be attacked by the immune system, or when functional efficacy of a patient's own cells, such as MSCs, are degraded or lost, such as in diseased or aged populations, and thus are non-viable for certain cell therapies.

Due to the tunable nature of the described particles, artificial cells, e.g., artificial MSCs, can be utilized in any application in which controlled release of factors produced by cells, such as MSCs is required. This can include but is not limited to cell therapy, tissue engineering, immunotherapy, treatment of inflammatory disorders or disorders involving bone loss, etc.

In one aspect, cellular (e.g. MSC) secreted factors are first obtained by administering fresh culture media to a near confluent flask of cells, such as MSCs, and returning the cells to an incubator to undergo additional culture. During this time, cells, e.g. MSCs, secrete potent factors and thereby "condition" their media. After several days, the now conditioned media is collected and utilized for subsequent encapsulation within polymeric, e.g. poly(lactic-coglycolic acid), particles. In one aspect, to achieve a desirable release pattern (e.g., (1) the release of a complete set of factors and (2) the continued release of those factors over an established time course), several particle sub-populations are fabricated which constitute the entirety of artificial cells (e.g., MSCs), These consist of particles produced in a highly-porous formulation designed to achieve an immediate release of all factors but each sub-population of particles is tailored to a time delay to achieve a cumulative sustained release. This simultaneous release can also be achieved using less-porous formulations.

According to another aspect is the application of artificial cells, e.g., artificial MSCs, for vascular tissue engineering, namely, their use as a replacement for the autologous cells that would traditionally be utilized. According to one aspect, artificial cells, e.g., artificial MSCs, are produced and incorporated within a synthetic, biodegradable, elastomeric, polymer scaffold. The combination of artificial cells, e.g., artificial MSCs, plus scaffold is utilized in one aspect as a vascular replacement/graft to replace damaged or diseased vascular segments with healthy ones.

In addition to the aforementioned benefits that artificial cells, e.g. MSCs, provide (lack of immunological concerns, consistent functionality irrespective of patient demographics), this combination product is superior in terms of practicality and cost when compared to many current tissue engineered vascular grafts. In particular, as autologous cells are no longer required, additional procedures do not need to be performed on patients as a means to isolate cells or suitable vascular segments. In addition, artificial cells, e.g., MSCs, can be created in substantial quantity in advance and subsequently stored allowing them to be applied in emergency situations. This is superior as compared cellular approaches which could require weeks of cell culture to obtain appropriate quantities. As such, the artificial cells are amenable to large-scale commercial preparation, distribution, and can be highly-standardized.

In one aspect, artificial MSCs are vacuum-seeded from the lumen outward into a porous elastic polymer tube. The seeded tube could then be stored or directly implanted. In one aspect, a porous polymer tube is prepared from a suitable biodegradable polymer composition by any method, e.g., by electrospinning or TIPS, and may comprise one or more concentric layers with one layer having a first composition and/or physical structure, and a second layer having a second composition and/or a second physical structure. For example, a first layer may be produced by a TIPS method, and a second layer may be electrodeposited about (e.g. concentrically around) the first layer. To "seed" the construct with the artificial cells described herein, a vacuum is applied to first side of the layers and the artificial cells are deposited on the opposite side of the layers, such that the artificial cells are sucked into the matrix of the layers. Likewise, increased pressure on one side of the layers would force artificial cells placed on the same side of the layers into the matrix.

According to one aspect of the invention, a method of preparing a controlled-release composition is provided comprising: culturing cells in cell culture medium, optionally for at least one hour, for example, from one hour to two weeks, including increments therebetween, such as: 1, 2, 3, 6, 8, 12, 18, or 24 hours, 1, 2, 3, 4, 5, 6, 7, 8, 9, 10, 11, 12, 13, or 14 days, and increments therebetween, e.g., from 1 to 4, or from 1 to 5 days, and increments therebetween, thereby producing conditioned medium. Next, collecting the conditioned medium. Optionally concentrating the conditioned medium, for example and without limitation by freezing and lyophilizing the medium and reconstituting the medium in a volume smaller than the original volume of medium collected from the cell culture, to produce a medium concentrate, that is, for example, 2×, 3×, 4×, 5×, 10×, or 20×.

In one aspect, particles containing the conditioned medium that are capable of burst-release or sustained release of active agents are broadly-known and have any pharmaceutically-acceptable composition or structure. Such particles can be prepared by any useful method, as are broadly-known by those of ordinary skill in the art. In one aspect, the particles are prepared by cross-linking (e.g, spontaneous cross-linking with, for example and without limitation, alginate). In another aspect, the compositions are prepared by emulsification. An emulsion can be prepared, for example, by microfluidics, membrane emulsification, sonication, homogenization, or any useful emulsification method, such as the method described below. In one aspect an emulsion is formed by sonicating the conditioned medium in a volatile solvent (for example and without limitation, an organic solvent having a boiling point of less than 100° C., for example pentane, cyclopentane, hexane, cyclohexane, benzene, chloroform, diethyl ether, or dichloromethane), comprising a polymer to produce a micro-emulsion, followed by homogenizing the micro-emulsion in an aqueous phase, so that particles precipitate as the solvent evaporates. In one aspect, the conditioned medium is medium from culture of a stem cell, a progenitor cell, an immune cell, a secretory cell, or an islet cell. In another aspect, the conditioned medium is medium from culture of a mesenchymal stem cell, a macrophage or an islet cell. In one aspect, the polymer is a polyester or polyester-containing copolymer, such as a polylactic-co-glycolic) acid (PLGA); a polylactic acid) (PLA); a poly(trimethylene carbonate) (PTMC); poly(caprolactone) (PCL); a poly(glycolic acid) (PGA); or a poly(glycolide-co-trimethylenecarbonate) (PGTMC).

In another aspect of the invention, a composition is provided comprising a first particle, e.g, having a first diameter, average pore size, and/or porosity, and comprising a first composition, e.g. a polymer composition, comprising conditioned medium from a mesenchymal stem cell culture, and having a first release profile of the conditioned medium, e.g, in blood, water, PBS or saline. In one aspect, the composition further comprises a second particle different from the first particle, e.g., having a second diameter, average pore size, and/or porosity, and comprising a composition, e.g., a polymer composition, that is the same or different from the composition of the first particle, and comprising conditioned medium from a cell culture and has a second release profile of the conditioned medium, e.g., in blood, water, PBS or saline different from the first release profile, thereby producing an extended release profile, releasing effective amounts of conditioned medium beyond the first release profile. The composition also may optionally comprise one or more additional particles comprising conditioned medium from a cell culture and having a release profile of the conditioned medium, e.g., in blood, water, PBS or saline different from the first and second release profile, thereby further extending release of effective amounts of conditioned medium beyond the first and second release profile. Conditioned medium may be full strength (1×), diluted (<1×) or concentrated (>1×). In one aspect, the conditioned medium is concentrated. In another aspect, the conditioned medium is medium from culture of a stem cell, a progenitor cell, an immune cell, a secretory cell, or an islet cell for example, wherein the conditioned medium is medium from culture of a mesenchymal stem cell, a macrophage or an islet cell. In one aspect, the first polymer, and optionally the second and/or additional polymer is a polyester or polyester-containing copolymer, such as a poly (lactic-co-glycolic) acid (PLGA); a poly(lactic acid) (PLA); a poly(trimethylene carbonate) (PTMC); poly(caprolactone) (PCL); a poly(glycolic acid) (PGA); or a poly(glycolide-co-trimethylenecarbonate) (PGTMC). In one aspect, the conditioned media of the second and/or one or more additional particles is medium from culture of a stem cell, a progenitor cell, an immune cell, a secretory cell, or an islet cell. For example, wherein the conditioned medium of the first, second, and/or one or more additional particles is medium from culture of a mesenchymal stem cell, a macrophage or an islet cell.

In another aspect, a controlled release pharmaceutical device, such as a controlled release implant, comprising conditioned media is provided. In a further aspect, the device comprises a polymer in which the conditioned media is distributed or otherwise contained. By "distributed", it is not implied that the conditioned media is evenly or uniformly distributed throughout the polymer. Controlled-release devices are broadly-known and range from compositions in which an active agent (e.g., the conditioned media described herein) is evenly-distributed, mixed with, absorbed into, adsorbed to, encapsulated within, layered within, or any other physical arrangement as are known in the pharmaceutical arts. Controlled release devices may include suitable carriers—that is "excipients", as are broadly-known. An excipient is an inactive substance used as a carrier for the active ingredients of a medication. Although "inactive," excipients may facilitate and aid in increasing or otherwise controlling or affecting the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

In another aspect of the invention, a device, e.g. a tissue growth scaffold, is provided comprising a porous, biocompatible polymer, and a first particle, e.g. having a first diameter, average pore size, and/or porosity, and comprising a first composition, e.g. a polymer composition, comprising conditioned medium from a cell culture, such as a mesenchymal stem cell culture, and having a first release profile of the conditioned medium, e.g. in blood, water, PBS or saline. In one aspect, the composition further comprises a second particle different from the first particle, e.g., having a second diameter, average pore size, and/or porosity, and comprising a composition, e.g. a polymer composition, that is the same or different from the composition of the first particle, and comprising conditioned medium from a cell culture and has a second release profile of the conditioned medium, e.g, in blood, water, PBS or saline different from the first release profile, thereby producing an extended release profile, releasing effective amounts of conditioned medium beyond the first release profile. The composition also may optionally comprise one or more additional particles comprising conditioned medium from a cell culture and having a release profile of the conditioned medium, e.g. in blood, water, PBS or saline different from the first and second release profile, thereby further extending release of effective amounts of conditioned medium beyond the first and second release profile.

In another aspect, the conditioned medium according to any aspect of the invention described herein is medium from culture of a stem cell, a progenitor cell, an immune cell, a secretory cell, or an islet cell for example, wherein the conditioned medium is medium from culture of a mesenchymal stem cell, a macrophage or an islet cell.

In one aspect, the tissue growth scaffold is a tube or tubular having a uniform or non-uniform cross-section, for example mimicking the shape of a tubular tissue, such as a vein, artery, esophagus, intestine, or other tubular anatomical structure. In another, it is a sheet. In yet another aspect, the tissue growth scaffold has a shape of an anatomical feature, such as a heart valve, muscle, cartilage, bone, etc.

In one example, a blood vessel growth scaffold is provided comprising a porous tube of a biocompatible polymer and a first particle, e.g, having a first diameter, average pore size, and/or porosity, and comprising a first composition, e.g, a polymer composition, comprising conditioned medium from a mesenchymal stem cell culture, and having a first release profile of the conditioned medium in, e.g., blood, water, PBS or saline. In one aspect, the composition further comprises a second particle different from the first particle, e.g., having a second diameter, average pore size, and/or porosity, and comprising a composition, e.g., a polymer composition, that is the same or different from the composition of the first particle, and comprising conditioned medium from a cell culture and has a second release profile of the conditioned medium in, e.g., blood, water, PBS or saline different from the first release profile, thereby producing an extended release profile, releasing effective amounts of conditioned medium beyond the first release profile. The composition also may optionally comprise one or more additional particles comprising conditioned medium from a cell culture and having a release profile of the conditioned medium in, e.g., blood, water, PBS or saline different from the first and second release profile, thereby further extending release of effective amounts of conditioned medium beyond the first and second release profile. In another aspect, the biocompatible polymer of the porous tube is bioerodible.

In use, the described tissue or blood vessel growth scaffold is implanted in a patient at a site of tissue to be replaced or anastomosed to a blood vessel or other tubular tissue. Thus provided according to one aspect of the invention is a method of producing tissue, such as blood vessel, in a patient, comprising implanting a tissue growth scaffold, or a blood vessel growth scaffold according to any aspect described herein in a patient.

In addition to the conditioned medium, other active agents may be incorporated into the particles, controlled-release devices, and/or tissue growth scaffold into which the particles are distributed, e.g. by mixing into the conditioned medium prior to incorporation into the particles, or by adsorption to or absorbance into the particles. As indicated above, the active agents may be growth factors, cytokines chemoattractants, and/or inflammation regulators, used to supplement the conditioned medium to tailor the cellular response, deposition, growth and other aspects of the tissue remodeling process as it occurs on the artificial growth scaffolds described herein. Specific examples of active agents, include: a growth factor, a small molecule, a cytokine, drug, a biologic, a protein or polypeptide, a chemoattractant, a binding reagent, an antibody or antibody fragment, a receptor or a receptor fragment, a ligand, or an antigen and/or an epitope. Specific examples of active agents include interleukins (IL), such as IL-2 and IL-12 (e.g., IL-12 p70), and interferons (IFN), such as IFN-γ.

Additional active agents that may be incorporated into the particles and/or growth scaffold include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, anti-inflammatory cytokines, and anti-inflammatory proteins or steroidal anti-inflammatory agents); antibiotics; anticlotting factors such as heparin, Pebac, enoxaparin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethasone, dexamethasone, flumethasone, isoflupredone, methylprednisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, bevacizumab, neovastat; (3) anti-proliferatives such as sirolimus, paclitaxel, perillyl alcohol, farnesyl transferase inhibitors, FPTIII, L744, anti-proliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, nitrates, nitrites, Diethylamine NONOate, Diethylamine NONOate/AM, Glyco-SNAP-1, Glyco-SNAP-2, S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, ofloxacin, ampicillin, amphotericin B, atovaquone, azithromycin, ciprofloxacin, clarithromycin, clindamycin, clofazimine, dapsone, diclazuril, doxycycline, erythromycin, ethambutol, fluconazole, fluoroquinolones, foscarnet, ganciclovir, gentamicin, itraconazole, isoniazid, ketoconazole, levofloxacin, lincomycin, miconazole, neomycin, norfloxacin, ofloxacin, paromomycin, penicillin, pentamidine, polymyxin B, pyrazinamide, pyrimethamine, rifabutin, rifampin, sparfloxacin, streptomycin, sulfadiazine, tetracycline, tobramycin, trifluorouridine, trimethoprim sulfate, Zn-pyrithione, and silver salts such as chloride, bromide, iodide and periodate.

Further examples of additional active agents include: basic fibroblast growth factor (bFGF or FGF-2), acidic fibroblast growth factor (aFGF), nerve growth factor (NGF), vascular endothelial growth factor (VEGF), hepatocyte growth factor (HGF), transforming growth factor-beta pleiotrophin protein, midkine protein, platelet-derived growth factor (PDGF) and angiopoietin-1 (Ang-1). Active agents are included in the delivery system described herein, and are administered in amounts effective to achieve a desired end-point, such as angiogenesis, tissue growth, inhibition of tissue growth, or any other desirable end-point.

In one aspect, a tissue growth scaffold is provided, such as a tubular structure suitable for replacement of a blood vessel, esophagus, intestine, or any other tubular anatomical structure. In another aspect, the tissue growth scaffold is formed as a sheet. In yet another aspect, the tissue growth scaffold is formed in a three-dimensional sheet. A variety of methods are available to form such structures, such as Thermally Induced Phase Separation (TIPS) methods and Non-solvent Induced Phase Separation (NIPS), which is useful for production of porous polymer structures. Additionally, high-resolution 3D printing technologies can deposit materials with microscale resolution, permitting highly-organized structures.

One useful method for producing the tissue structures and/or controlled-release devices is electrodeposition. The polymeric scaffold can be electrospun, e.g., on a mandrel in the case of a tubular tissue scaffold, e.g, a vascular tissue. The particles can be added to the tissue scaffold by concurrent electrospraying, or by vacuum, as described elsewhere herein. Electrospinning permits fabrication of scaffolds that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in anisotropic scaffolds. These aligned scaffolds can influence cellular growth, morphology and ECM production. For example, Ku et al. found smooth muscle cell (SMC) alignment with poly(L-lactide-co-ε-caprolactone) fibers (Xu C. Y., et al. "Aligned biodegradable nanofibrous structure: a potential for blood vessel engineering", Biomaterials 2004 (25) 877-86.) and Lee et al. submitted aligned non-biodegradable polyurethane to mechanical stimulation and found cells cultured on aligned scaffolds produced more ECM than those on randomly organized scaffolds (Lee C. H., Shin H. J., Cho I. H., Kang Y. M. Kim I. A., Park K. D., Shin, J. W., "Nanofiber alignment and direction of mechanical strain affect the ECM production of human ACL fibroblast", Biomaterials 2005 (26) 1261-1270).

Generally, the process of electrospinning involves placing a polymer-containing fluid (e.g, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrospinning, the polymer-containing fluid is charged by the application of high voltage to the solution or orifice (e.g., about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (e.g., 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh (matrix) is formed on the biased target.

The properties of the electrospun elastomeric matrices can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain embodiments, the biased target is moved back and forth in a regular, periodic fashion, such that fibers of the non-woven mesh are substantially parallel to each other. When this is the case, the resulting non-woven mesh may be anisotropic, e.g., having a higher resistance to strain in the direction parallel to the fibers, compared to the direction perpendicular to the fibers. In other embodiments, the biased target is moved randomly relative to the orifice, so that the resistance to strain in the plane of the non-woven mesh is isotropic. The target can also be a rotating mandrel. In this case, the properties of the non-woven mesh may be changed by varying the speed of rotation. The properties of the electrospun elastomeric scaffold may also be varied by changing the magnitude of the voltages applied to the electrospinning system.

Electrospinning may be performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, a mandrel may be used as a target.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without any intention to be limited by this theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component include from about 1% wt. to about 15% wt., from about 4% wt. to about 10% wt. and from about 6% wt. to about 8% wt.

Thickness of the matrix can be controlled by either adjusting the viscosity of the polymer composition to be deposited and/or adjusting duration of the electrospinning. Use of more viscous polymer composition may result in thicker fibers, requiring less time to deposit a matrix of a desired thickness. Use of a less viscous polymer composition may result in thinner fibers, requiring increased deposition time to deposit a matrix of a desired thickness. The thickness of the matrix and fibers within the matrix affects the speed of bioerosion of the matrix. These parameters are optimized, depending on the end-use of the matrix, to achieve a desired or optimal physiological effect.

TIPS can be combined with electrospinning. For example, a tubular vascular scaffold can be manufactured by first producing a tubular inner layer using TIPS, and then electrospinning a second layer about the circumference of the inner layer to provide improved structural strength. In such a structure, it may be desirable to disperse the particles into the scaffold by vacuum (e.g., by RVSD) as described below.

Polymeric particles comprising conditioned media, that is, the artificial cells described herein, may be distributed in or on a scaffold structure by any method, such as by spraying, electrospraying, vacuum deposition, pressure deposition, absorption, adsorption, etc. In one aspect, the artificial cells are co-deposited by spraying concurrently with electrodeposition of the scaffolding. In another aspect, the artificial cells are distributed into the scaffolding by applying a vacuum or pressure differential to the scaffold that forces a solution containing the artificial cells to enter the scaffold.

The cells that are used to provide conditioned media for use in the particles described herein include, without limitation, stem cells, progenitor (precursor) cells, smooth muscle cells, skeletal myoblasts, myocardial cells, endothelial cells, endothelial progenitor cells, bone-marrow derived mesenchymal cells, neural cells, glial cells, and neuronal and glial progenitor cells, chondrocytes and progenitors thereof, osteogenic cells (e.g., osteoclasts) and progenitors thereof, and genetically modified cells. In certain embodiments of the genetically-modified cells, the genetically modified cells are capable of expressing a therapeutic substance, such as a growth factor. Examples of suitable growth factors include angiogenic or neurotrophic factor, which optionally may be obtained using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors (IGF), transforming growth factor-beta pleiotrophin protein, midkine protein. A large variety of genetically modified cells that might be used to produce conditioned media, and the methods of making and using those cells are known or can be developed readily by an ordinary artisan.

EXAMPLES

Example 1

Vascular grafts that are currently used in small-diameter arterial bypass or in AV access for dialysis are not ideal and have significant failure rates. Tissue-engineered vascular grafts (TEVGs) using autologous mesenchymal stem cells (MSCs) show promise, but have two main limitations that may prevent their clinical translation. First, patients at high risk for cardiovascular disease—such as the elderly and diabetics—have dysfunctional MSCs which may not be able to yield a viable TEVG. Second, the use of any cell type that requires extended culture expansion—including MSCs—opens the door to the risk of cellular contamination or transformation; as well as high costs and a substantial waiting time before a TEVG can be fabricated. The overall goal of the work is to develop a novel, clinically-viable, rapidly-fabricated, cell-free TEVG. Secreted factors from human MSCs can be harvested, packaged, and delivered by compositions, such as the "artificial MSCs" (artMSCs) described herein, that can then replace the paracrine activity of the MSCs in our TEVG.

A therapy based on secreted factors from standardized human MSC cell lines (i.e., from healthy patients) offers a uniform treatment strategy from patient to patient than an inherently variable autologous cell-based strategy. The cell-free nature of this approach is more easily translatable to the clinic, and the cost and time spent harvesting cells from individual patients would be eliminated.

The artMSCs are designed to encourage four processes: i) prevention of acute thrombosis; ii) chemotaxis of active host cells into the TEVG; iii) proliferation and spreading of vascular cells, and iv) synthesis of extracellular matrix. By combining these aspects—the design, optimization and fabrication of artMSCs—with TEVG methods, including rotational vacuum seeding device (RVSD) (Soletti L, et al., A seeding device for tissue engineered tubular structures. Biomaterials 27, 2006) and elastomeric polyester urethane) urea (PEUU) scaffold (Nieponice A, et al., In vivo assessment of a tissue-engineered vascular graft combining a biodegradable elastomeric scaffold and muscle-derived stem cells in a rat model. Tissue Engineering Part A 16, 2010; Soletti L, et al., A seeding device for tissue engineered tubular structures. Biomaterials 27; 2006; Nieponice A, et al., Development of a tissue-engineered vascular graft combining a biodegradable scaffold; muscle-derived stem cells and a rotational vacuum seeding technique. Biomaterials 29, 2008; Soletti L, et al., A bilayered elastomeric scaffold for tissue engineering of small diameter vascular grafts. Acta Biomater. 6, 110, 2010)—a clinically-translatable, "off-the-shelf" TEVG for use in arterial bypass and replacement becomes achievable. The methods, devices and compositions provided herein address critical barriers to clinical translation such as the cellular transformation and cost associated with in vitro expansion, and the difficulty of providing a uniform TEVG for all patients, especially those at high risk of cardiovascular disease.

Here, conditioned media from human MSCs from a healthy population (i.e. non-diabetic, non-elderly) is harvested and encapsulated within PLGA particles (FIG. 1).

Harvest of Conditioned Media from Human MSCs

Adult human MSCs are purchased from a commercial vendor (RoosterBio, Frederick, Md.), with the restriction that source donors must be adults under 45 years old (to avoid the potential for deficits in MSC from elderly patients (Krawiec J T, et al., A cautionary tale for autologous vascular tissue engineering: Impact of human demographics on the ability of adipose-derived mesenchymal stem cells to recruit and differentiate into smooth muscle cells. Tissue Engineering Part A, 2014; Madonna R, et al., Age-dependent impairment of number and angiogenic potential of adipose tissue-derived progenitor cells. European journal of clinical investigation 41, 2011; Zhu M, et al., The effect of age on osteogenic, adipogenic and proliferative potential of female adipose-derived stem cells. Journal of tissue engineering and regenerative medicine 3, 2009; Schipper B M, et al., Regional anatomic and age effects on cell function of human adipose-derived stem cells. Annals of plastic surgery 60, 2008) and non-diabetic. To harvest conditioned media, flasks of nearly confluent (~80%) MSCs between passages 4 and 7 are given fresh media, and allowed to condition it for 48 hours, after which it is harvested. Media is snap frozen to fully preserve biologically active factors and stored at −80° C.

Scratch Wound Assay for SMC and EC Migration

Media conditioned by MSC from healthy donors promotes migration of SMC—an essential function for in-vivo remodeling of TEVGs—in a scratch wound healing assay (Krawiec J T, et al., A cautionary tale for autologous vascular tissue engineering: Impact of human demographics on the ability of adipose-derived mesenchymal stem cells to recruit and differentiate into smooth muscle cells. Tissue Engineering Part A, 2014). We utilize the same assay here. In short, human aortic SMCs (ATCC), or in separate experiments human aortic ECs (Lonza), are plated and grown to confluence on glass chamber slides (Lab-Tek). After removing the culture media the monolayer is disrupted by a single stroke scrape with a 40 µL pipette tip. Scraped monolayers are washed in 1×HBSS and incubated with media containing 1 µL/mL of Cell Tracker Red (Invitrogen, #C34552) to load the cells for fluorescent visualization, Non-conditioned MSC media is used as a control for unstimulated migration. Images are collected to assess the relative wound area every 2 hours using a Live Cell fluorescent microscopic system (Nikon ECLIPSE Ti, Photometrics CoolSNAP HQ2, Plan Apo 20×DIC M N2, NIS Elements 4.0) over a total of 24 hours. Cells remain under typical cell culture conditions for this duration (20% $O_2$/5% $CO_2$/37° C.). Migration rate is determined based on relative area of wound closure.

Figure 2:
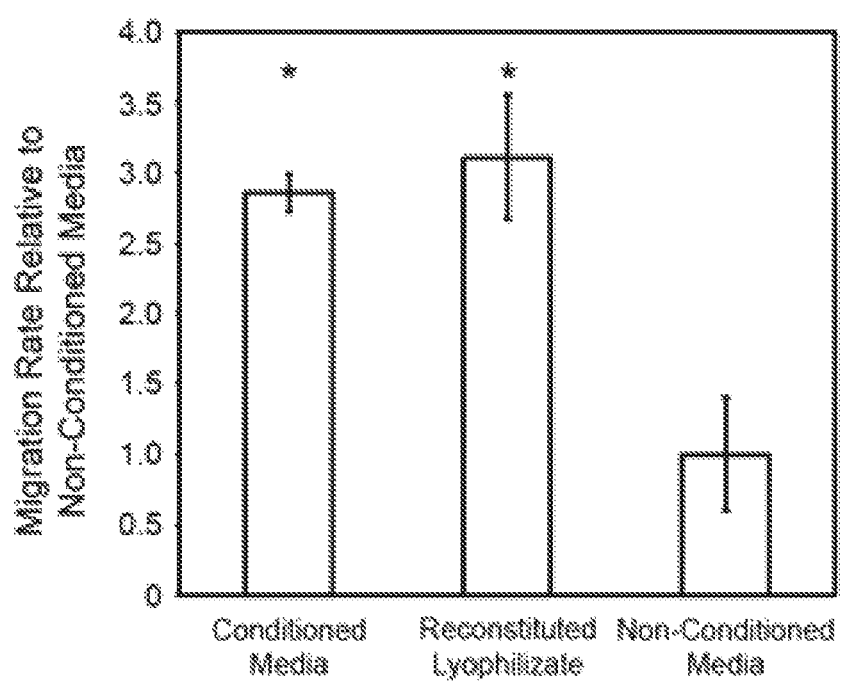
FIG. 2 shows that lyophilized and reconstituted media retains activity in SMC migration assay. Media conditioned by MSC was lyophilized, reconstituted to the original volume with ultrapure water, then used in a SMC migration assay as described herein (mean±SD, n=3 per group; *=p<0.05 vs, non-conditioned). Positive and negative controls were conditioned media that was not lyophilized and media that was not conditioned, respectively.

Human MSC conditioned media can promote the migration of SMCs, and can identify differences between MSC donor groups (e.g., diabetic vs non-diabetic, aged vs young, etc.). This assay is used to validate the chemotactic activity of conditioned media from the commercial MSC (FIG. 2).

Concentration of MSC Conditioned Media to Control Dosage

In order to achieve equivalent biological activity to a batch of conditioned media, the particles forming the artMSCs preferably encapsulates a relatively concentrated solution of secreted factors. This is because the volume of encapsulated media within particles is only a fraction compared to the total volume of their surrounding solution, yet they must release a high enough concentration of factors to achieve a functionally relevant dose. To concentrate the media, it is frozen and lyophilized, followed by resuspension in sterile ultrapure water. Determining the correct ratio of resuspension volume to particle volume is an iterative process—a range of ratios is evaluated for particle release assays and the ratio that best replicates the concentration of factors and biological activity of conditioned media is selected.

To verify that we can concentrate conditioned media from humans, and retain its biological activity, we performed the following experiment. Three different samples of conditioned media were lyophilized, and each was reconstituted into a smaller volume to gain a 13-fold concentration with reliable repeatability (original concentration 647±4 µg/mL, lyophilized/reconstituted concentration: 8639±129 µg/mL, n=3). The lyophilized media samples were then re-diluted to their original concentrations, and then used in a SMC migration assay. We determined from the results of this assay that the conditioned media retained its pro-migratory effect on SMCs even after lyophilization (FIG. 2).

Encapsulating MSC Conditioned Media in Particles

Particles are fabricated using an established double emulsion procedure from an organic solution of PLGA (a readily-translatable, biocompatible, and biodegradable polymer which is FDA approved for drug delivery) in dichloromethane (DCM). In this technique, the aqueous phase, consisting of conditioned media, either in its original or reconstituted form after concentrating; is micro-emulsified in the organic phase via sonication (FIG. 3). The second emulsion occurs using homogenization in a larger aqueous phase. As the solvent evaporates, the solid polymer precipitate forms spherical particles, which are then lyophilized and stored at −20° C. until use. Particle size and morphology are determined using volume impedance measurements and scanning electron microscopy, respectively.

The process above has been known to (under certain circumstances) reduce the biological activity of proteins. However, the above procedure was used successfully in the experiment described below, where conditioned media from MSC was encapsulated in PLGA particles, using porous and non-porous configurations to ensure that the artMSCs can be tuned to effectively release encapsulated contents while maintaining biological activity.

Release of Conditioned Media

After MSC conditioned media is encapsulated within particles, the particles are allowed to release their cargo in ultrapure water (100 µl water per µl of particles) in an incubator at 37° C. Control particles are fabricated using either saline or non-conditioned media. At a given time point, the particle suspension is mixed and centrifuged before withdrawing a 10 µL sample of the supernatant. An additional 10 µL of water is added back to the suspension before returning it to the incubator to preserve the total volume. Samples are withdrawn, e.g., over the course of two weeks (1, 3, 5, 7, 10, 12, 14 days). In addition to the assays described below for MSC secreted factor quantification and biological activity, the total protein content of each sample is measured using the bicinchoninic acid (BCA) assay (Walker J M. The bicinchoninic acid (BCA) assay for protein quantitation. *The protein protocols handbook.* Springer; 2009:11-15).

Figure 4:
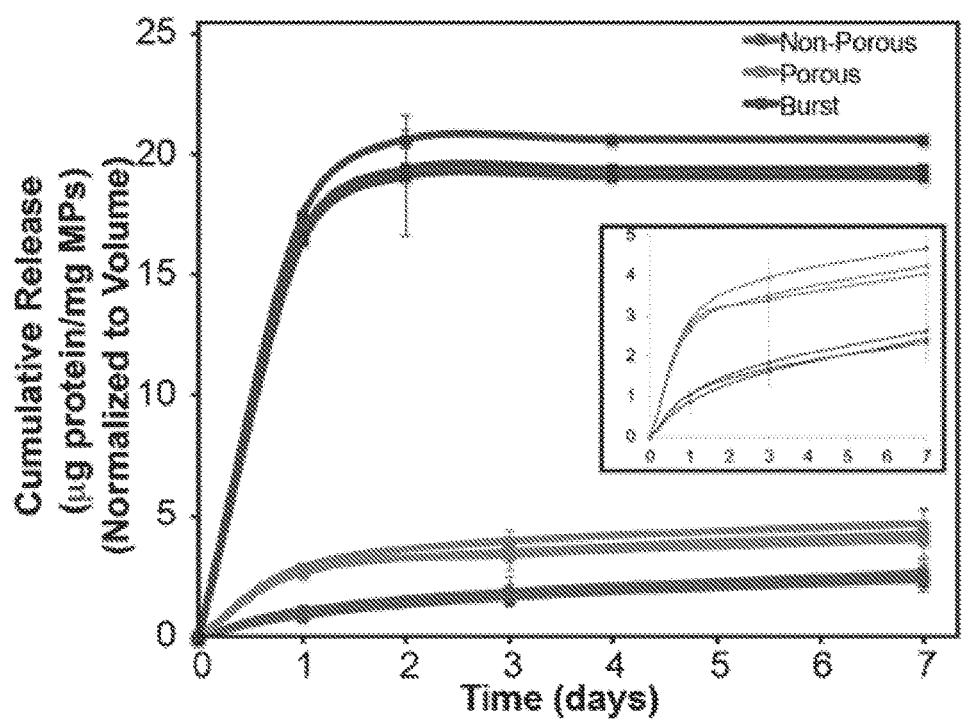
FIG. 4 shows release profiles. PLGA particles were fabricated using three different configurations (non-porous, porous, and burst) as described herein. In all cases, MSC conditioned media was encapsulated. Releasates were harvested daily and total protein content of each sample was measured by the BCA assay. Cumulative protein release was then plotted over the seven day period, to illustrate the three different release profiles (mean±SD, n=3 per group).

Data demonstrates that we are capable of developing distinct release profiles utilizing MSC-conditioned-media-loaded particles fabricated with non-porous and increasingly porous configurations using a double emulsion procedure. As can be seen in FIG. 4, release is tunable by an order of magnitude as well as by as little as 2-fold by simply varying the porosity of the particles. It is also possible to tune the ratio of the amount delivered within the first two days compared to the amount delivered over the first week of release. The most appealing release is the "burst" configuration, by which all molecules can be released in concert. Alternative systems that do not fully deliver their cargo can often exclude certain factors based on size, resulting in drastically different functional effects. Utilizing the "burst" configuration allows delivery of the entire combination of secreted factors, fully imparting the beneficial effects of MSCs.

Analysis of Representative Biologically Relevant MSC Factors in Releasates

ELISAs are performed on samples withdrawn from media conditioned by healthy MSCs and particle releasates according to the manufacturer instructions. Representative factors to be investigated are VEGF, MCP-1, BDNF, and uPA. These factors were chosen since all four are known to be among the secretory products of MSCs in vitro which are involved with aspects or mechanisms of TEVG remodeling (e.g., smooth muscle cell (SMC) migration, monocyte recruitment, angiogenesis, anti-thrombogencity, etc.).

To demonstrate the ability to generate and release relevant bioactive factors produced by MSCs, releasates from particles encapsulated with conditioned media (concentrated, "burst formulation") were analyzed, VEGF and uPA, which regulate host cell migration into the TEVG and anti-thrombogenicity, respectively, were released at 712 pg VEGF/mL and 8 pg uPA/mL, respectively. This concentration of VEGF (~1 ng/mL) has been shown in vitro to be able to stimulate SMC migration.

Biological Validation of Media Activity: SMC/EC Migration and Proliferation

To ensure that the conditioned media maintains its activity after encapsulation (i.e. similar to the retained activity after lyophilization, FIG. 2), the samples obtained above are taken and two biological activity assays: a scratch wound assay to look at effects on SMC and EC migration, and an immunostaining assay to look at SMC and EC proliferation (details below) are performed. In either case, the activity of the releasates is compared to the same volume of conditioned media, and potent release will be defined as equivalent activity to the media control. Releasates from particles loaded with saline or non-conditioned media also are analyzed.

Short term-controlled proliferation is desirable and necessary to repopulate and remodel our TEVG. To this end, SMC and EC are cultured for 1, 4, and 7 days in the presence of particle releasates (or media conditioned by MSC as controls) and their proliferative state is investigated by immunofluorescent staining. An antibody to Ki67 (Abcam), a well-established marker for proliferating human cells, is used to determine if proliferation is increased beyond non-conditioned media controls. It is noted that extended proliferation of vascular cells—particularly SMCs—could be detrimental to graft success and lead to neointimal hyperplasia. To this point, it is noted that we have performed explants of MSC-based TEVGs at 1, 2, 4, 8, 12, and 52 weeks and never encountered intimal hyperplasia.

While PLGA is typically considered a biocompatible material (Athanasiou K A, Niederauer G G, Agrawal C M. Sterilization, toxicity, biocompatibility and clinical applications of polylactic acid/polyglycolic acid copolymers. Biomaterials 17, 1996), a small amount of acid is produced as a byproduct of PLGA particle degradation, and this could either detrimentally affect the activity of the MSC factors or be toxic to cells in the microenvironment. A "check" for this is built into the experimental approach—in the former case a decrease in SMC migration would be seen, relative to MSC conditioned media alone, and in the latter we would observe that releasates from saline-loaded particles have a negative impact on EC/SMC proliferation. Methods of troubleshooting polymer formulations for particles available. Among such techniques is the addition of a carrier protein such as BSA or PEGylation to protect the activity of the therapeutic cargo (Divan M, Park T G. Pegylation enhances protein stability during encapsulation in plga microspheres. J. Control. Release 73, 2001). Fabrication methods also can be adapted for use of PLGA copolymers with hydrophilic materials such as alginate or the inclusion of antacid excipients (Schwendeman S P. Recent advances in the stabilization of proteins encapsulated in injectable plga delivery systems. Critical Reviews™ in Therapeutic Drug Carrier Systems 19, 2002). Similarly, insufficient loading can be addressed by making modifications to the fabrication process, such as increasing the drug-to-polymer ratio or reducing the stirring rate.

TEVG remodeling is a dynamic process, whether the implanted graft is fully synthetic, fully biological, or a hybrid of the two. Because remodeling occurs within the host, the process is something of a "black box". In the case of our MSC-based TEVGs, the cells seeded into the scaffold prior to implantation are gone by 8 weeks, and whether they have migrated from the graft or simply died is unknown. Since the intent of the artMSC concept is to deliver inductive factors produced by the MSC, it will be helpful to first learn when the MSC are present during the remodeling process (and thus delivering factors) and how soon vascular cells are recruited from the host. Therefore, we—A) determine the time course of the TEVG remodeling for an MSC seeded construct, and B) fine-tune families of particles to release MSC derived factors over the entire time that MSC are present. Iterative optimizations beyond the initial formulation are tuned to achieve the appropriate in vivo release kinetics, which may not necessarily correlate to in vitro release behavior. In silica design methods should produce a first attempt that closely approximates the desired input, and the dynamic measurement of levels of VEGF, MCP-1, BDNF, and uPA will guide the fine-tuning to achieve a rapid optimization.

Seeding of PEUU Scaffolds

Rat sized tubular, biodegradable, elastomeric scaffolds (1.3 mm ID, 10 mm length, ~390 µm TIPS thickness, ~70 µm ES thickness) are seeded with MSCs. The material used for the scaffold is polyester urethane)urea (PEUU), a polymer which has been developed and extensively characterized, and which offers substantial customizability with respect to pore size, porosity, and mechanical properties. PEUU is fabricated into a tubular geometry. In short, PEUU scaffolds are fabricated by using thermal-induced phase separation (TIPS) to create an inner, porous layer to facilitate cell seeding and integration, and by finishing with an electrospun (ES) outer layer to provide mechanical stability. The mechanical properties of ES-TIPS PEUU scaffolds are very attractive: a burst pressure similar to the human saphenous vein and a suture retention force greater than the porcine internal mammary artery (Soletti L, et al., A bilayered elastomeric scaffold for tissue engineering of small diameter vascular grafts. Acta Biomater, 6, 110, 2010), Additionally, TEVGs constructed with this scaffold have shown minimal inflammation and no signs of mechanical failure or dilation after a year of implantation in a rat model (unpublished preliminary data).

Figure 5:
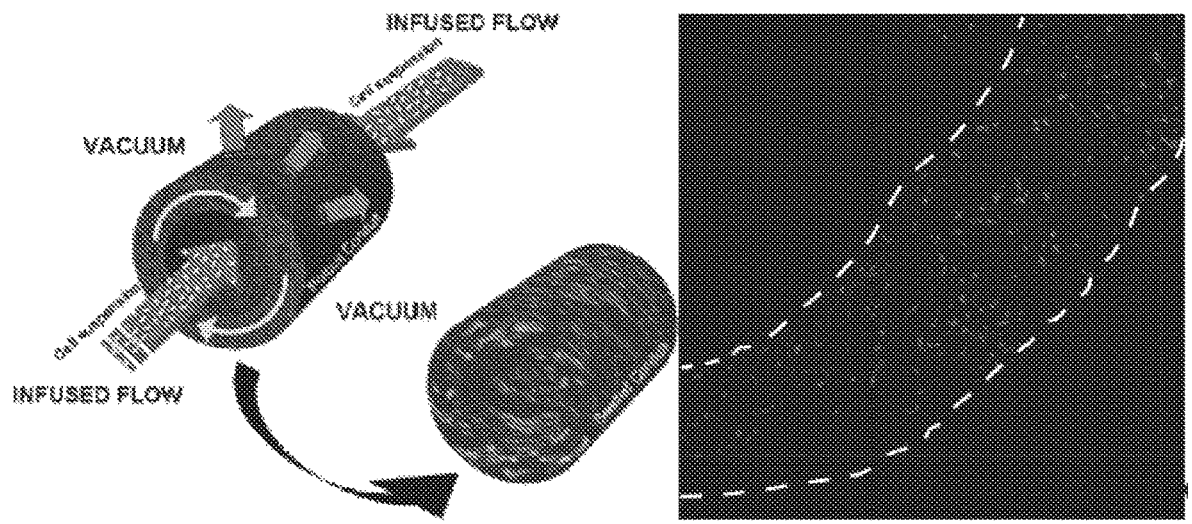
FIG. 5 shows that vacuum seeding results in evenly distributed cells. The Rotational Vacuum Seeding Device functions by infusing a cell suspension through the lumen of the PEUU scaffold upon which a vacuum and rotation are applied to uniformly distribute the cells. This technique offers a rapid (<5 min), highly efficient (>90%), uniform, and repeatable bulk seeding process. Uniform seeding is highlighted by the image on the right, which shows cellular nuclei (blue) within a PEUU scaffold (borders marked with dashed lines). Left image adapted from Soletti L, et al., A seeding device for tissue engineered tubular structures. Biomaterials 27, 2006.

MSCs are seeded into PEUU scaffolds utilizing a Rotational Vacuum Seeding Device (RVSD) (FIG. 5) (Soletti L, et al., A seeding device for tissue engineered tubular structures. Biomaterials 27, 2006; Nieponice A, et al., Development of a tissue-engineered vascular graft combining a biodegradable scaffold, muscle-derived stem cells and a rotational vacuum seeding technique. Biomaterials 29, 2008). Based on preclinical data in utilizing these techniques, a scaffold seeded with 3 million MSC, cultured for 2 days in a spinner flask (15 rpm) to achieve even cell attachment and spreading, then implanted in a rat model regenerated into a TEVG of native-like tissue after 8 weeks (Nieponice A, et al., In vivo assessment of a tissue-engineered vascular graft combining a biodegradable elastomeric scaffold and muscle-derived stem cells in a rat model. Tissue Engineering Part A 16, 2010).

Figure 6:
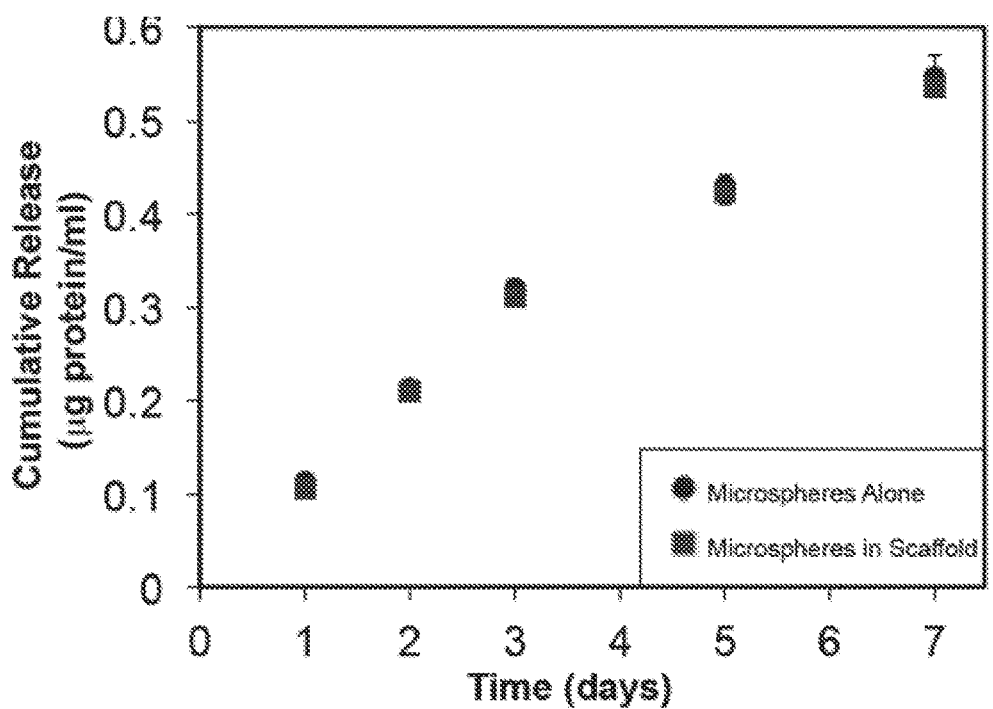
FIG. 6 shows that particle release is unaffected by seeding. Particles were vacuum-seeded into PEUU scaffolds, assayed by BCA as described, and compared to release from particles alone (mean±SD, n=3 per group).

The total protein release profiles from batches of artMSCs and from PEUU scaffolds seeded with equal amounts of the same artMSCs was measured, and were found to be indistinguishable (FIG. 6).

In Vivo Implantation in a Rat Model

Scaffolds seeded with 3 million human MSC (n=4 per group) and prepared as described above are implanted as abdominal aortic interposition grafts in Lewis rats—an inbred strain with minimal immune rejection of implanted human cells. Utilizing this model with human cells immunological complications were not encountered; at both 1 and 8 weeks, explants show no signs of lymphocyte activity, and at 52 weeks there were no signs of gross inflammation.

Implantation follows established and previously-described protocols (He W, et al., Pericyte-based human tissue engineered vascular grafts. Biomaterials 31, 2010; Hibino N, et al., A critical role for macrophages in neovessel formation and the development of stenosis in tissue-engineered vascular grafts. The FASEB Journal 25, 2011; Nieponice A, et al., In vivo assessment of a tissue-engineered vascular graft combining a biodegradable elastomeric scaffold and muscle-derived stem cells in a rat model. Tissue Engineering Part A 16, 2010; Soletti L, et al.; In vivo performance of a phospholipid-coated bioerodable elastomeric graft for small-diameter vascular applications. Journal of Biomedical Materials Research Part A 96, 2011) (see Vertebrate Animals section). The longest implantation time point is 8 weeks, since at that time point we already know from extensive preliminary data that there is full recellularization with host cells and no sign of the seeded cells. The strategy is to narrow down the relevant window where MSCs are actively participating in the remodeling process. Implantations are first employed at the middle time point (4 weeks), then establish the next time points based on those results. Four events to be detected are 1) the disappearance of MSC, 2) the appearance of SMC, 3) the appearance of EC, and 4) the appearance of vascular ECM.

120 seeded scaffolds have been implanted in rats, using a variety of cell types: rat smooth muscle cells, rat muscle derived stem cells (MDSCs), human pericytes, and human MSCs from healthy, diabetic, and elderly donors. Consistently, substantial EC and SMC recruitment as well as collagen and elastin content is present at the 8 week timepoint. It should be noted that non-cell seeded grafts display very poor patency.

Explant Characterization

To examine the composition of the explanted TEVGs, immuno-fluorescent chemistry (IFC) is used following previously established protocols (He W, et al., Pericyte-based human tissue engineered vascular grafts. Biomaterials 31, 2010; Nieponice A, et al., In vivo assessment of a tissue-engineered vascular graft combining a biodegradable elastomeric scaffold and muscle-derived stem cells in a rat model. Tissue Engineering Part A 16, 2010) and morphometric measurements such as number of cells expressing a protein, or area covered by the expressing cells, are measured. IFC is performed investigating the presence of smooth muscle alpha actin, calponin, and myosin heavy chain to assess for SMCs. von Willebrand Factor and CD31 is used to determine the presence of ECs. To assess the ECM components, antibodies against collagen type I, collagen type III, and elastin are used.

Inflammation, which was previously thought to solely be a negative effect, is actually important in physiologic vascular remodeling. To investigate the type of inflammation present in TEVGs and to ensure no gross inflammation exists that could compromise them, IFC is performed utilizing antibodies for the total number of macrophages (CD68) and to classify the type of inflammation (M1 CCR7; M2: CD163). To detect an innate immune response (B-cells and T-cells) CD54RA (AbD Serotec, #MCA340G) antibody is used.

The presence of residual human MSCs is monitored in order to define the necessary timeframe for our artMSCs. An anti-human nuclear antibody (Millipore, #MAB1281) is used to visualize the cells via IFC.

Figure 7:
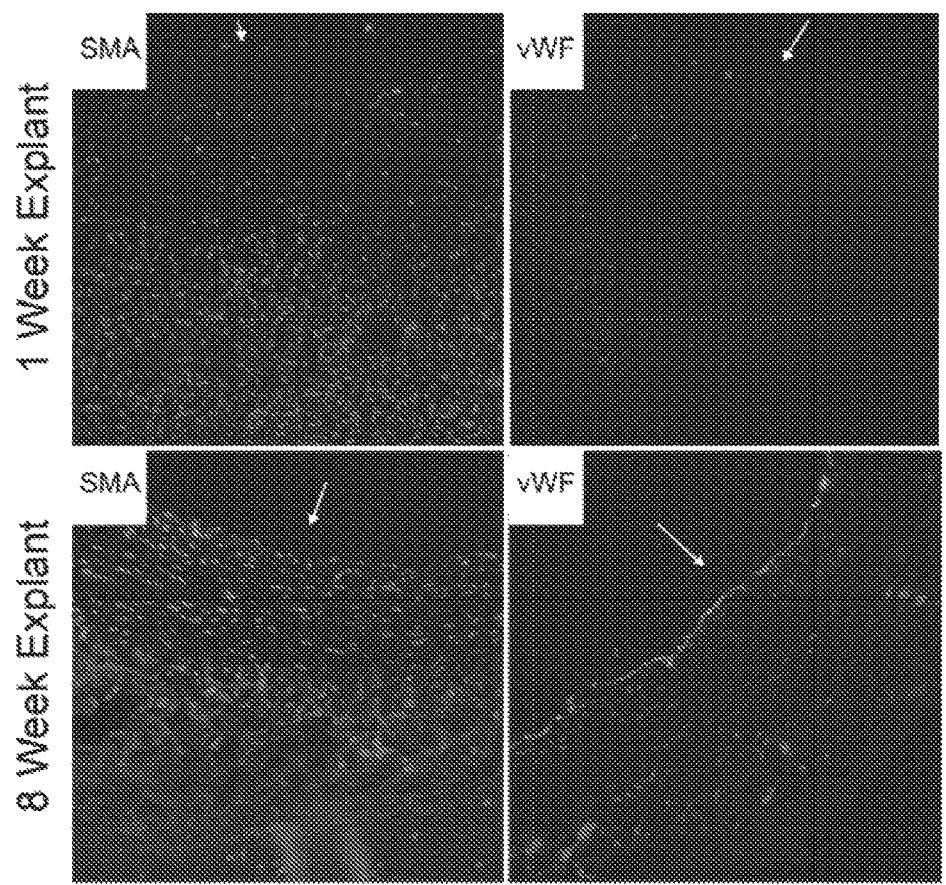
FIG. 7 illustrates TEVG recellularization is minimal at 1 week and is complete after 8 weeks. PEUU scaffolds seeded with MSC were implanted as described herein and explanted after 1 week (n=2) for comparison to 8 week explants examined in previous and ongoing work (He W, et al., Pericyte-based human tissue engineered vascular grafts. Biomaterials 31, 2010; Nieponice A, et al., In vivo assessment of a tissue-engineered vascular graft combining a biodegradable elastomeric scaffold and muscle-derived stem cells in a rat model. Tissue Engineering Part A 16, 2010; Krawiec J T, et al., Human diabetic adipose stem cells display reduced fibrinolysis due to urokinase activity attributing to their pro-thrombogenic phenotype Under Review, 2015; Krawiec J T, et al., In vivo functional evaluation of tissue engineered vascular grafts fabricated using human adipose-derived stem cells. Under Review, 2015). After explantation, the vessels were analyzed by IFC for the SMC marker smooth muscle alpha-actin (SMA) or the EC marker von Willebrand Factor (VWF). Recellularization is incomplete after 1 week of implantation, but complete by 8 weeks, Note that the IFC data is representative of the explants at both timepoints.

Human MSC-based explant data at 1 week shows the initial recruitment of SMC, but not EC. In contrast, there is significant recellularization by both SMC and EC at 8 weeks (FIG. 7).

Modification of artMSCs to Mimic the In Vivo Activity of Implanted MSCs

Figure 9:
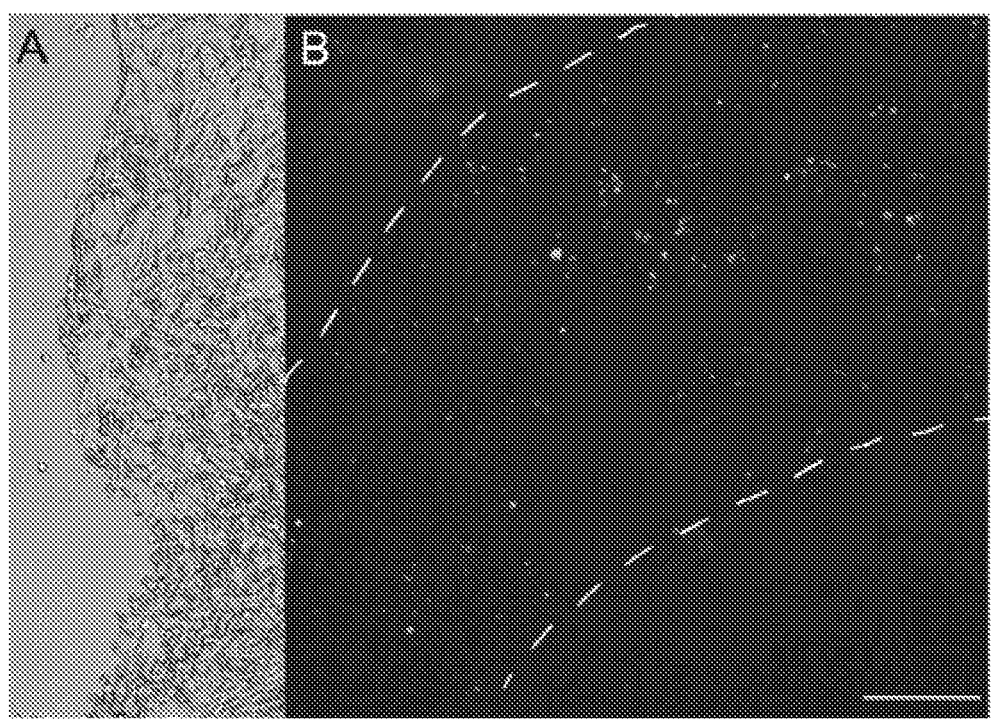
FIG. 9 shows that 5 µm artMSC can be seeded into PEUU scaffolds, and are retained after implantation. A) PLGA particles (average diameter=20 µm) were seeded into a PEUU scaffold, imaged and characterized using the methods described. On average, the particles within the scaffold (pseudocolored gray for clarity) were 5 µm in diameter. B) Scaffolds seeded with FITC-loaded particles were implanted as described and explanted after 3 days (n=2). Upon sectioning and imaging, FITC particles were noted throughout the thickness (outer and inner borders of scaffold marked with dashed lines).

A particle system capable of releasing conditioned media (e.g., all secreted factors) from human MSCs is described herein. The particles are engineered such that the timing of their "burst-release" (wherein all factors from conditioned media will be delivered) is tunable. The method for tuning such a delayed burst is illustrated in FIG. 9 along with preliminary data. A single "burst" would not last long enough to cover the entire duration that MSC are present. Instead populations of differently-tuned particles that will each release after a programmed delay were fabricated to cover the time of MSC presence.

Based on the success of preliminary studies to date, the primary parameter that is varied to achieve temporally distinct burst releases is porosity, which preliminary studies suggest allows for a wide range of release behavior within the appropriate levels. Other influencing factors, such as polymer molecular weight (which correlates to degradation rate of the particles) and inner occlusion size (which can be controlled independent of surface porosity to program a delayed burst, as seen in FIG. 4), also is accounted for when generating these well-defined families. Ultimately, the optimized combination of these different families and numbers of particles per family are chosen such that they reflect the activity seen in vivo. As an example; if the number of MSCs is high in our early implant times and then decreases over time, a higher number of particles from the earlier releasing families and less of the late releasing families are incorporated in our mixture.

ELISA to Verify Factors in Releasates from artMSC Families

Figure 8:
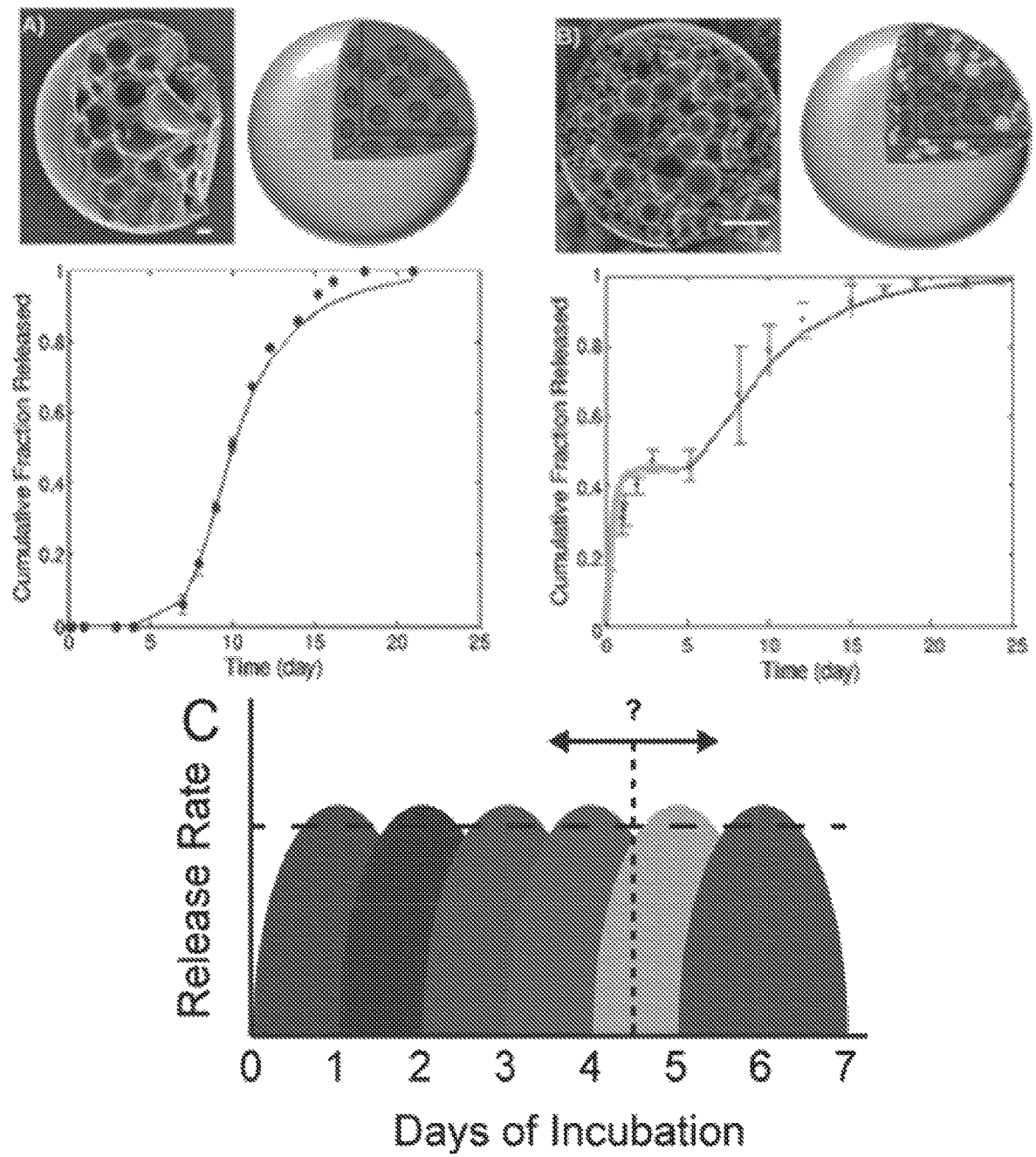
FIG. 8 shows how matrix architecture can dictate how much (if any) encapsulated drug will be released in an "initial burst". A) Matrix with no connection between drug-loaded pockets and its surface yields no initial burst. B) A network of pores connects a subdomain of the drug-loaded pockets to the matrix surface, leading to a corresponding initial burst (mean±SEM, n=3 per group in A and B). C) Proposed release profile from multiple particles, each having different release profiles as illustrated by the two different particles of FIGS. 8A and 8B.

Releasates are obtained from the desired mix of delayed-release artMSCs families as above, and are screened as above to determine if the release of secreted factors is indeed prolonged. Successful families of artMSC will maintain a high level of release of factors up to the point determined above (e.g., the vertical line in FIG. 8C), after which the factors will cease.

It is noted that certain factors may be added to the concentrated conditioned medium if it is later found that additional amounts of the specific factor is needed when using the described composition in a real-world setting. The amounts of the additional specific factor effective to accommodate this can be determined empirically.

Verification of Seeding of Multiple Families of artMSC

The PEUU scaffold for the TEVG has a porous inner layer with an average pore size of 50 µm; which supports infiltration by host cells and allows graft remodeling. To mimic the seeding of MSC, the artMSC are blk-seeded at the same density—3 million particles per scaffold—using RVSP. (pilot studies were performed to determine what size particles to use as artMSCs, wherein a range of sizes were tested to assess optimal retention in the scaffold; see below). Seeded constructs are sectioned and analyzed via microscopy to determine seeding density, with the goal being that seen with a gold standard MSC-based TEVG.

In order to validate that families of artMSC (with different programmed delayed-payload-release) seed equally well, pairs of particle families having different tuning configurations are loaded with contrasting fluorophores, FITC and Rhodamine. Seeded scaffolds are sectioned and imaged under fluorescent microscopy, determining the quantity and distribution of each color particle per scaffold. We expect that the various families will all seed in a similar fashion.

To determine the diameter of particles that will enter a PEUU scaffold and remain embedded there, a preparation of porous PLGA particles with multiple sizes (average diameter=20 μm) was used. Some particles in the mixture were able to both infiltrate the scaffold and remain within the pores despite several washes in preparative buffer. The size of the particles within the porous structure of the scaffold was found to be, on average, 5 μm, while particles on the order of 10 μm or more remained excluded from the porous layer (FIG. 9). After noting that particles were not dislodged from scaffolds upon subjection to physiologic flow conditions in vitro, implantation of FITC particle seeded scaffolds was performed. After three days in vivo under physiological flow, the particles remained within the scaffold (FIG. 9).

Implant of artMSC TEVG and Explant Analysis

ArtMSC-seeded constructs are implanted into a rat model following the same procedures and testing as above. Explantation occurs at 8 weeks so that the performance of the ArtMSC-based TEVGs can be compared to the large set of results that we have accumulated over the years with cell-based TEVGs at that same time point. This comparison is based on patency, cellular composition (EC, SMC and inflammatory cells), ECM composition, and mechanical properties as described below.

Patency is assessed by placing a catheter into the descending thoracic aorta where a contrast agent is delivered to the graft and visualized under X-ray upon euthanasia. Patency is calculated as the number of open TEVGs (which allow contrast agent to pass through) as a percentage of total number of TEVGs. Following this the TEVGs are explanted and characterized for their composition.

Composition is assessed according to the cellular components investigated above, and using the same techniques. In addition, to assess the extracellular matrix components mainly found in the vasculature, antibodies against collagen type I, collagen type III, and elastin are used.

Mechanical properties such as strength and compliance are critical to how a TEVG functions and performs but there has been relatively little investigation into the mechanical properties of explanted TEVGs. Dynamic compliance is measured by placing the explanted TEVG in our ex vivo vascular perfusion system using previously established protocols to measure pressure (P) and outer diameter (D) of the TEVG during pulsatile perfusion (Soletti L, et al., A bilayered elastomeric scaffold for tissue engineering of small diameter vascular grafts. Acta Biomater. 6, 110, 2010). Dynamic compliance is calculated as (D120−D80)/(D80* (P120−P80)) from measures of D and P at systolic (120) and diastolic (80) pressures. Following compliance testing the TEVGs are cut into 3 rings and tested uniaxially using established protocols on an Instron Tensile Tester (#5543A) (Soletti L, et al., A bilayered elastomeric scaffold for tissue engineering of small diameter vascular grafts. Acta Biomater. 6, 110, 2010). UTS is defined as the maximum stress the sample experienced before tensile failure.

Initial assessments of healthy MSC-based TEVG explants demonstrate that the mean uniaxial tangent modulus within the physiologic range (80-120 mmHg) is similar to the native artery at both 2 and 8 weeks (0.44, 0.56, and 0.44 MPa for 2 week explant, 8 week explant, and native artery, respectively).

Figure 10:
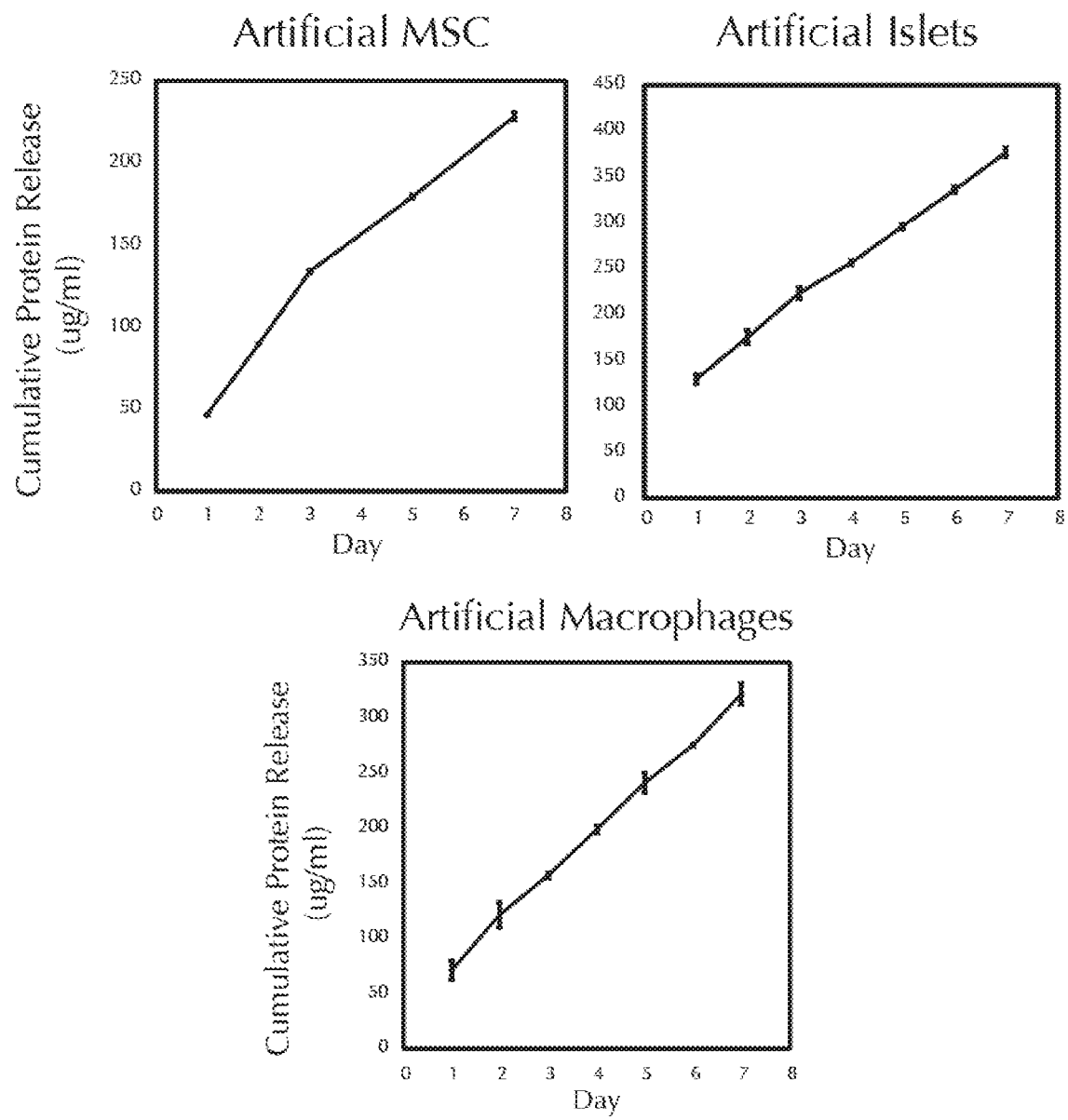
FIG. 10 shows that media conditioned by mesenchymal stem cells (MSC), islet cells, and macrophages can be encapsulated within particles and released in a controlled manner. Data suggests that media conditioned by multiple cell types can be released from our particle system and therefore that this technology could serve as the foundation of many types of "artificial cells".

Cells were grown to 80% confluence and then used to condition fresh media for 48 hours. The 48 hour conditioned media was then collected, concentrated via lyophilization and resuspension, and packaged into PLGA particles. Particles equivalent to 1 mL of conditioned media were then incubated in phosphate buffered saline to allow release of secreted factors. Aliquots of releasates were measured daily for protein concentration by bicinchoninic acid assay and then plotted as a cumulative release over seven days. These data (FIG. 10) suggest that media conditioned by multiple cell types can be released from the described particle system and therefore that this technology could serve as the foundation of many types of "artificial cells".

Protocol:
1. Each cell type was cultured to 80% confluence
2. The media was then removed and fresh media applied for 48 hours
3. The conditioned media was then collected and centrifuged at 1200 rpm for 5 minutes and the supernatant was collected and frozen at −80° C.
4. The supernatant was then lyophilized and re-suspended at a 10× concentration in PBS
5. The concentrated media was then encapsulated in PLGA particles
6. The final mass of the particles was then measured and the mass per volume of encapsulated media was determined
   0.05866 g particles=10 mL encapsulated media
   0.0058 g particles=1 mL
7. 1 mL encapsulated media (0.0058 g of particles) was then released into 1 mL of PBS at 37° on a shaker plate for 7 days
8. Every 24 hours, the mixture was centrifuged and the supernatant (which contains the particle releasates) was removed and frozen at −80° C. until use. 1 mL new PBS was applied to the remaining particles to create an "infinite sink" environment
9. After 7 days of release from the particles, the releasates were thawed and the concentration of released protein in each sample was measured using a BCA assay.

Example 2: Using Artificial Stem Cells in Making a Vascular Conduit

Methods:
1) Harvest of Conditioned Media from Human MSCs

Adult human MSCs between passages 4 and 7 are cultured to near confluence (~80%) and then are given fresh culture media. After 48 hours (during which the cells condition the media with secreted factors) the media is removed, centrifuged to remove cell debris, and snap frozen. If concentration of the conditioned media is desired for encapsulation, the frozen media can be lyophilized and resuspended using a smaller volume of distilled water.

2) Fabrication of Artificial MSCs

Microspheres are fabricated using a double emulsion procedure from an organic solution of PLGA (a readily-translatable, biocompatible, and biodegradable polymer which is FDA approved for drug delivery) in dichloromethane and an aqueous solution comprised of the conditioned media. First, the conditioned media is micro-emulsified in the organic phase via sonication. Second, the mixture is added to a larger aqueous phase and homogenized. As the solvent evaporates, the solid polymer precipitate forms spherical particles, which are then lyophilized and stored at −20° C. until use.

3) Seeding of Vascular Scaffolds

Tubular, porous, biodegradable, elastomeric scaffolds (for a rat-implantable geometry, 1.3 mm ID, 10 mm length) are lumenally vacuum-seeded with artificial MSCs. Poly(ester urethane)urea-based scaffolds work well for this purpose, but other polymers can be used. A vacuum pressure of 120 mmHg results in even seeding of artificial MSCs with an average size of 20 μm.

4) In Vivo Implantation in a Rat Model

Scaffolds seeded with 6 million artificial MSCs are surgically implanted into Lewis rats in the infrarenal abdominal aorta position as described below, Rats are placed under anesthesia (Isofluorane 1%, ketamine (50 mg/kg as needed)) after which a midline incision is made and the abdominal aorta exposed. Microclamps are applied to the infrarenal aorta and both common iliac arteries. The seeded scaffold is then sutured to replace the native aorta as an end-to-end anastomosis with interrupted 10-0 prolene sutures. After the graft is secured, the clamps are released. Following observation of pulsatile blood flow through the scaffold, the muscle and skin layers can then be closed with 4-0 polyglactin resorbable sutures. Antibiotic therapy is advised prior to surgery (cefazolin—100 mg/kg, intramuscular) and for three days post-surgery (Baytril—10 mg/kg, oral, twice daily). Analgesics (buprenorphine—0.5 mg/kg, subcutaneous, twice daily for 3 days) and anticoagulants (dipyridamole—250 mg/kg for the first 7 days, 100 mg/kg for the following 3 weeks, oral; aspirin—200 mg/kg for the first 7 days, 100 mg/kg for the following 3 weeks, oral) are also be administered post-surgery.

Expected Results:

1) Patency

By analogy to scaffolds seeded with MSCs, we expect a high patency rate of the artificial MSC-seeded scaffolds at 8 weeks post-implantation. Patency can be measured using angiography as follows. The animal is sedated (or euthanized) and placed under X-ray imaging while a catheter is maneuvered into the descending thoracic artery, A contrast agent (such as Renograf) is injected from the catheter and imaged as it travels through the proximal aorta, graft, and distal aorta. Full flow through the graft is scored as full patency. In larger animals, other non-invasive techniques could be used to assess graft patency including in vivo ultrasound. Gross patency can also be observed after explant and cross-sectioning of the explanted graft.

2) Composition

The native aorta is composed mainly of lumenal endothelial cells, medial smooth muscle cells, and extracellular matrix structures such as collagen and elastic fibers. Over 8 weeks, MSC-seeded scaffolds remodel into a vessel-like tissue containing all of these features. We expect that artificial MSC-seeded scaffolds will also remodel, and this can be measured by the following assays. First, the explanted graft is be cut into histological sections for immunologic staining; antibodies to detect endothelial cells (CD31, von Willebrand Factor), smooth muscle cells (alpha smooth muscle actin, calponin, and smoothelin), collagen (type I and III), and elastic fibers (elastin, fibrillin-1, fibrillin-2, and others) are readily available. Second, sections can be histologically stained by Masson's or Lillie's trichrome, picrosirius red, and Verhoeff Van Gieson stains to look at various extracellular matrix features.

3) Mechanical Properties

The extracellular matrix composition and organization in the native aorta is primarily responsible for its passive mechanical properties. Over the course of remodeling of MSC-seeded scaffolds, the passive mechanical properties change from that of the scaffold polymer into properties resembling the native aorta. Several techniques are available to compare the ultimate mechanical properties of artificial MSC-seeded scaffolds (after 8 weeks of implant) to the native aorta. First, the explanted graft can be cannulated and exposed to pulsatile lumenal ex vivo while simultaneously monitoring flow, lumenal pressure, and diameter. These measurements allow calculation of vessel compliance. Second, cross sectional rings and longitudinal strips can be cut from the explanted vessel to allow uniaxial tensile testing—these measurements can provide information of directional elastic modulus and ultimate tensile strength. Burst pressure and suture retention strength can also be tested post-explant.

Example 3: Bioactivity of the Artificial Stem Cells Using a Scratch Wound Assay

Methods:

1) Collection of the Artificial Stem Cell Releasates 3 mg of microspheres (mass seeded into each scaffold) are released into 1 mL of PBS. Each releasate sample is put into an end-over-end rocker for 24 hours. After 24 hours of release, each releasate sample is spun down at 1000 rpm in the centrifuge. The supernatant is isolated and considered to be to the microsphere releasates.

2) Culture of Smooth Muscle Cells

Human aortic smooth muscle cells (SMCs) purchased from ATCC are plated at 100,000 cells per well in a six well plate and grown to 80% confluency.

3) Scratch Wound

Once cells reach confluence, a scratch wound is administered using a pipette tip. Each slide is then rinsed in 1×HBSS and incubated with media containing 1 µL/mL of Cell Tracker Red (Invitrogen, #C34552) to fluorescently label the cells. The media is then aspirated and the releasates applied. Non-conditioned MSC media acts as a control for migration. Cells are imaged every 2 hours for 24 hours using a Live Cell fluorescent microscope system (Nikon ECLIPSE Ti, Photometrics CoolSNAP HQ2, Plan Apo 20×DIC M N2, NIS Elements 4.0). Migration is then quantified through rate of wound closure (i.e., rate of decrease of cell-void area on slide).

Expected Results:

Previous preliminary data (FIG. 2) detected bioactive factors within conditioned media via a scratch assay. Successful loading and release of conditioned media from microspheres was measured using a total protein assay (FIG. 7). The proposed scratch assay aims to confirm the bioactivity of the media being released from the microspheres.

1) Basal Media Control

Standard SMC cell media will be used as a negative control. Since we hypothesize the paracrine factors present within conditioned media are the driving force behind smooth muscle cell migration, unconditioned media is expected to promote no significant migration of the cells into the scratch wound while still maintain cell viability.

2) Conditioned Media

As previously shown (FIG. 2), conditioned media successfully promotes the migration of SMCs and will act as a positive control.

3) Artificial MSC Releasates

Since we have proven the pro-migratory effects of conditioned media and its successful loading and release from microspheres, we expect to observe SMC migration and wound closure comparable to that of conditioned media.

The following clauses are illustrative of various aspects of the invention:

A composition comprising a first particle comprising conditioned medium from a cell culture within the particle, and having a first release profile of the conditioned medium, optionally in blood, water, PBS or saline.

1. The composition of clause 1, further comprising a second particle different from the first particle, comprising conditioned medium from a cell culture within the particle and having a second release profile of the conditioned medium, optionally in blood, water, PBS or saline, different from the first release profile, thereby producing an extended release profile, releasing effective amounts of the conditioned medium beyond (e.g., prior to, after; or overlapping with) the first release profile, wherein the conditioned medium of the first and second particles are the same or different.
2. The composition of clause 2, further comprising one or more additional particles, each independently comprising conditioned medium from a cell culture within the particle and having a release profile of the conditioned medium, optionally in blood, water, PBS or saline, different from the first and second release profile, thereby further extending release of effective amounts of the conditioned medium beyond the first and second release profile, wherein the conditioned medium of the first, second, and one or more additional particles are the same or different.
3. The composition of any one of clauses 1-3, wherein the particles comprise a polymer material, a ceramic material, or a material capable of osmotic release.
4. The composition of one of clauses 1-4, wherein the conditioned medium is medium from culture of a stem cell, a progenitor cell, an immune cell, a secretory cell; or an islet cell
5. The composition of any one of clauses 1-5, wherein the conditioned medium is medium from culture of a mesenchymal stem cell, a macrophage or an islet cell.
6. The composition of any one of clauses 1-6, wherein the particles comprise a polymer.
7. The composition of any one of clauses 1-7, wherein the particles comprise a polyester or polyester-containing copolymer, such as a polylactic-co-glycolic) acid (PLGA); a poly(lactic acid) (PLA); a poly(trimethylene carbonate) (PTMC); poly(caprolactone) (PCL); a poly(glycolic acid) (PGA); or a poly(glycolide-co-trimethylenecarbonate) (PGTMC).
8. A tissue growth scaffold comprising a porous material of a biocompatible polymer and a composition as defined in any one of clauses 1-8.
9. The tissue growth scaffold of clause 8, wherein the biocompatible polymer is bioerodible, such as a poly(ester urethane) urea (PEUU); poly(ether ester urethane) urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-methylene carbonate-co-dioxanone).
10. The tissue growth scaffold of clause 9 or 10, wherein scaffold is a tube or a sheet.
11. A blood vessel growth scaffold comprising a porous tube of a biocompatible polymer and a composition as defined in any one of clauses 1-8.
12. The blood vessel growth scaffold of clause 12, wherein the biocompatible polymer is bioerodible, such as a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).
13. A method of making a tissue growth scaffold comprising distributing a composition of any one of clauses 1-8 in a biocompatible polymer.
14. The method of clause 14, wherein the biocompatible polymer is bioerodible, such as a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy adds such as: polylactide, poly(lactide-co-glycolide), poly(L-lactide-co-caprolactone), polyglycolic acid; poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).
15. A controlled release pharmaceutical device comprising conditioned medium.
16. The device of clause 16, wherein the conditioned medium is medium from culture of a stem cell, a progenitor cell, an immune cell; a secretory cell, or an islet cell.
17. The device of clause 16, wherein the conditioned medium is medium from culture of a mesenchymal stem cell, a macrophage or an islet cell.
18. The device of any one of clauses 16-18, wherein the device comprises a polymer in which the conditioned medium is distributed.
19. The device of any one of clauses 16-19, wherein the device comprises a polyester or polyester-containing copolymer, such as a poly(lactic-co-glycolic) acid (PLGA); a poly(lactic acid) (PLA); a poly(trimethylene carbonate) (PTMC); poly(caprolactone) (PCL); a poly(glycolic acid) (PGA); or a poly(glycolide-co-trimethylenecarbonate) (PGTMC).
20. A method of preparing a controlled-release composition comprising:
 a. culturing cells in cell culture medium, optionally for at least one hour, for example, from one hour to two weeks, including increments therebetween, such as: 1, 2, 3, 6, 8, 12, 18, or 24 hours, 1, 2, 3, 4, 5, 6, 7, 8, 9, 10, 11, 12, 13, or 14 days, and increments therebetween up to one week and 1-5 days and increments therebetween, thereby producing conditioned medium;
 b. collecting the conditioned medium;
 c. optionally concentrating the conditioned medium;
 d. emulsifying, for example by sonicating, the medium in a volatile solvent (e.g., an organic solvent having a boiling point less than 100° C., for example pentane, cyclopentane, hexane; cyclohexane, benzene, chloroform, diethyl ether, or dichloromethane), comprising a polymer to produce a micro-emulsion; and
e. homogenizing the micro-emulsion in an aqueous phase, so that particles precipitate as the solvent evaporates.
21. The method of clause 21, wherein the conditioned medium is concentrated, for example and without limitation by freezing and lyophilizing the medium and reconstituting the medium in a volume smaller than the original volume of medium collected from the cell culture, to produce a medium concentrate, that is, for example, 2×, 3×, 4×, 5×, 10×, or 20×.
22. The method of clause 21 or 22, wherein the conditioned medium is medium from culture of a stem cell, a progenitor cell, an immune cell, endothelial cells, smooth muscle cells, a secretory cell, or an islet cell, for example the conditioned medium is medium from culture of a mesenchymal stem cell, a macrophage or an islet cell.
23. The method of any one of clauses 21-23, wherein the polymer is a polyester or polyester-containing copolymer, such as a poly(lactic-co-glycolic) acid (PLGA); a poly (lactic acid) (PLA); a poly(trimethylene carbonate) (PTMC); poly(caprolactone) (PCL); a poly(glycolic acid) (PGA); or a poly(glycolide-co-trimethylenecarbonate) (PGTMC).
24. A method of producing tissue, such as blood vessel, in a patient, comprising implanting a tissue growth scaffold according to claim 7 in a patient.

Having described this invention, it will be understood to those of ordinary skill in the art that the same can be performed within a wide and equivalent range of conditions, formulations and other parameters without affecting the scope of the invention or any embodiment thereof.

We claim:

1. A tissue growth scaffold comprising a porous material of a biocompatible polymer and a composition comprising:
a first particle comprising a first conditioned medium from a cell culture within the first particle, and having a first release profile of the first conditioned medium; and
a second particle, different from the first particle, comprising a second conditioned medium from a cell culture within the second particle, and having a second release profile of the second conditioned medium different from the first release profile,
wherein the first conditioned medium is the same as or different than the second conditioned medium,
wherein a combination of the first particle and the second particle produces an extended release profile, releasing effective amounts of the first and/or second conditioned medium beyond the first release profile.

2. The tissue growth scaffold of claim 1, wherein the biocompatible polymer is a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from polylactide, poly(lactide-co-glycolide), poly(L-lactide-co-caprolactone), polyglycolic acid, poly(dl-lactide-co-glycolide), and/or poly (l-lactide-co-dl-lactide); a polymer comprising monomers derived from polyhydroxybutyrate, polyhydroxyvalerate, polydioxanone, and/or polyglactin; a polymer comprising monomers derived from lactones; or a polymer comprising monomers derived from polycarbonate, polyglyconate, poly(glycolide-co-trimethylene carbonate), or poly(glycolide-co-trimethylene carbonate-co-dioxanone).

3. The tissue growth scaffold of claim 1, wherein the scaffold is a tube or a sheet.

4. A blood vessel growth scaffold comprising a porous tube of a biocompatible polymer and a composition comprising:
a first particle comprising a first conditioned medium from a cell culture within the first particle, and having a first release profile of the conditioned medium; and
a second particle, different from the first particle, comprising a second conditioned medium from a cell culture within the second particle, and having a second release profile of the second conditioned medium different from the first release profile,
wherein the first conditioned medium is the same as or different than the second conditioned medium,
wherein a combination of the first particle and the second particle produces an extended release profile, releasing effective amounts of the first and/or second conditioned medium beyond the first release profile.

5. The blood vessel growth scaffold of claim 4, wherein the biocompatible polymer is a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from polylactide, poly(lactide-co-glycolide), poly(L-lactide-co-caprolactone), polyglycolic acid, poly(dl-lactide-co-glycolide), and/or poly (l-lactide-co-dl-lactide); a polymer comprising monomers derived from polyhydroxybutyrate, polyhydroxyvalerate, polydioxanone, and/or polyglactin; a polymer comprising monomers derived from lactones; or a polymer comprising monomers derived from polycarbonate, polyglyconate, poly(glycolide-co-trimethylene carbonate), or poly(glycolide-co-trimethylene carbonate-co-dioxanone).

6. A method of making a tissue growth scaffold comprising distributing a composition in a biocompatible polymer, the composition comprising:
a first particle comprising a first conditioned medium from a cell culture within the first particle, and having a first release profile of the conditioned medium; and
a second particle, different from the first particle, comprising a second conditioned medium from a cell culture within the second particle, and having a second release profile of the second conditioned medium different from the first release profile,
wherein the first conditioned medium is the same as or different than the second conditioned medium,
wherein a combination of the first particle and the second particle produces an extended release profile, releasing the effective amounts of the first and/or second conditioned medium beyond the first release profile in a biocompatible polymer.

7. The method of claim 6, wherein the biocompatible polymer comprises a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from polyhydroxybutyrate, polyhydroxyvalerate, polydioxanone, and/or polyglactin; a polymer comprising monomers derived from lactones; or a polymer comprising monomers derived from polycarbonate, polyglyconate, poly(glycolide-co-trimethylene carbonate), or poly(glycolide-co-trimethylene carbonate-co-dioxanone).

8. The method of claim 6, further comprising determining the first release profile and/or the second release profile is-deter-mined in blood, water, PBS or saline.

9. A method of preparing a controlled-release composition comprising:
   a) preparing a first particle by:
      i) culturing cells in a cell culture medium, thereby producing a first conditioned medium;
      ii) collecting the first conditioned medium;
      iii) emulsifying the first conditioned medium in a volatile solvent comprising a polymer to produce a micro-emulsion; and
      iv) homogenizing the micro-emulsion in an aqueous phase, so that particles precipitate as the solvent evaporates, to produce the first particle having a first release profile of the first conditioned medium;
   b) preparing a second particle by:
      i) culturing cells in a cell culture medium, thereby producing a second conditioned medium that is the same or different than the first cultured medium in the first particle;
      ii) collecting the second conditioned medium;
      iii) emulsifying the second conditioned medium in a volatile solvent comprising a polymer to produce a micro-emulsion; and
      iv) homogenizing the micro-emulsion in an aqueous phase, so that particles precipitate as the solvent evaporates, to produce the second particle having a second release profile of the second conditioned medium different than the first release profile; and
   c) incorporating the first and second particles into a tissue scaffold comprising a porous material comprising a biocompatible polymer,
   wherein a combination of the first particle and the second particle in the scaffold produces an extended release profile, releasing the effective amounts of the first and/or second conditioned medium beyond the first release profile.

10. The method of claim 9, further comprising concentrating the first and/or second medium after the collecting step and prior to the emulsifying step.

11. The method of claim 9, wherein the first and/or second conditioned medium is from culture of a stem cell, a progenitor cell, an immune cell, endothelial cells, smooth muscle cells, a secretory cell, or an islet cell.

12. The method of claim 9, wherein the polymer is a polyester or polyester-containing copolymer.

13. The method of claim 9, wherein steps a)iii) and b)iii) emulsifying of the medium in a volatile solvent comprising a polymer to produce a micro-emulsion comprise sonicating the medium in a volatile solvent comprising a polymer to produce the micro-emulsions.

14. The method of claim 10, wherein the first and/or second conditioned medium is concentrated by freezing and lyophilizing the first and/or second conditioned medium and reconstituting the first and/or second conditioned medium in a volume smaller than the original volume of first and/or second conditioned medium collected from the cell culture, to produce a first and/or second conditioned medium concentrate.

15. The method of claim 9, wherein the polymer is a poly(lactic-co-glycolic) acid (PLGA); a poly(lactic acid) (PLA); a poly(trimethylene carbonate) (PTMC); poly(caprolactone) (PCL); a poly(glycolic acid) (PGA); or a poly(glycolide-co-trimethylenecarbonate) (PGTMC).

16. The method of claim 11, wherein the first and/or second conditioned medium is from culture of a mesenchymal stem cell, a macrophage or an islet cell.

17. A method of producing tissue in a patient, comprising implanting a tissue growth scaffold according to claim 1 in a patient.

* * * * *

UNITED STATES PATENT AND TRADEMARK OFFICE
CERTIFICATE OF CORRECTION

PATENT NO. : 11,684,574 B2
APPLICATION NO. : 16/308889
DATED : June 27, 2023
INVENTOR(S) : Morgan Virginia Fedorchak et al.

It is certified that error appears in the above-identified patent and that said Letters Patent is hereby corrected as shown below:

On the Title Page

Column 1, Assignees, Lines 3-5, delete "(US); Svstem of Higher Education 1tts, Urgh (PA)" and insert -- (US) --

In the Specification

Column 1, Line 8, delete "Sates" and insert -- States --

In the Claims

Column 35, Line 3, Claim 8, after "profits" delete "is-deter-mined"

Signed and Sealed this
Twenty-ninth Day of August, 2023

Katherine Kelly Vidal
*Director of the United States Patent and Trademark Office*